(12) United States Patent
Morishita et al.

(10) Patent No.: US 8,772,449 B2
(45) Date of Patent: Jul. 8, 2014

(54) CELL-PENETRATING PEPTIDES

(75) Inventors: Mariko Morishita, Tokyo (JP); Kozo Takayama, Tokyo (JP); Reiji Nishio, Kamakura (JP); Nobuo Ida, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 124 days.

(21) Appl. No.: 13/321,176

(22) PCT Filed: May 19, 2010

(86) PCT No.: PCT/JP2010/058420
§ 371 (c)(1),
(2), (4) Date: Nov. 28, 2011

(87) PCT Pub. No.: WO2010/134537
PCT Pub. Date: Nov. 25, 2010

(65) Prior Publication Data
US 2012/0065124 A1    Mar. 15, 2012

(30) Foreign Application Priority Data
May 20, 2009   (JP) ................. 2009-122096
Mar. 26, 2010  (JP) ................. 2010-071774

(51) Int. Cl.
  *C07K 7/08*      (2006.01)
  *A61K 38/10*     (2006.01)
  *C07K 14/435*    (2006.01)
  *A61K 9/00*      (2006.01)

(52) U.S. Cl.
  CPC ............ *C07K 7/08* (2013.01); *C07K 14/43581* (2013.01); *A61K 38/10* (2013.01); *A61K 9/0053* (2013.01); *A61K 9/007* (2013.01); *A61K 9/0073* (2013.01)
  USPC ............ 530/326; 530/327; 530/328; 514/1.1; 514/21.4

(58) Field of Classification Search
  CPC .... C07K 7/08; C07K 14/43581; A61K 38/10; A61K 9/0053; A61K 9/007; A61K 9/0073
  USPC ................... 514/1.1, 21.4; 530/326, 327, 328
  See application file for complete search history.

(56) References Cited

FOREIGN PATENT DOCUMENTS

| EP | 1 559 724 A1 | 8/2005 |
| JP | 10-33186 A | 2/1998 |
| JP | 10-95738 A | 4/1998 |
| WO | WO 00/29427 A2 | 5/2000 |

OTHER PUBLICATIONS

Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Extended European Search Report for European Application No. 10777770.8 dated May 7, 2013.
Kamei et al., "Determination of the Optimal Cell-Penetrating Peptide Sequence for Intestinal Insulin Delivery Based on Molecular Orbital Analysis with Self-Organizing Maps," Journal of Pharmaceutical Sciences, vol. 102, No. 2, Feb. 2013, pp. 469-479.
Khafagy et al., "Effect of Cell-Penetrating Peptides on the Nasal Absorption of Insulin", Journal of Controlled Release, 133, (2009), pp. 103-108.
Khafagy et al., "Structural Requirements of Penetratin Absorption Enhancement Efficiency for Insulin Delivery", Journal of Controlled Release, 143, (2010), pp. 302-310.
Khafagy et al., "The role of Intermolecular Interactions with Penetratin and Its Analogue on the Enhancement of Absorption of Nasal Therapeutic Peptides", International Journal of Pharmaceutics, 388, (2010), pp. 209-212.
Search Report dated Aug. 24, 2010 for International Application No. PCT/JP2010/058420.
Terasawa et al., "Bio Yakubutsu no Koritsuteki Shokakan Kyushu o Mezasita Shinki Saibomaku Toka Peptide no Kaihatsu", Journal of Pharmaceutical Science and Technology, 2009, vol. 69, pp. 95.

* cited by examiner

*Primary Examiner* — Julie Ha
(74) *Attorney, Agent, or Firm* — Birch, Stewart, Kolasch & Birch, LLP

(57) ABSTRACT

A cell-penetrating peptide of (A) to (D) below gives cell membrane permeability and transmucosal absorbability to a physiologically active substance:
  (A) a peptide having the amino acid sequence of SEQ ID NO:1;
  (B) a peptide represented by SEQ ID NO:1 except that one or several basic amino acids are changed;
  (C) a peptide represented by SEQ ID NO:1 except that 1 to 5 amino acids are changed;
  (D) a peptide having: the reverse sequence of any of (A) to (C); an amino acid sequence which is the same as the reverse sequence of (A) except that one or several basic amino acids are changed; or an amino acid sequence which is the same as the reverse sequence of (A) except that 1 to 5 amino acids are changed.

5 Claims, 8 Drawing Sheets

CELL-PENETRATING PEPTIDES

TECHNICAL FIELD

The present invention relates to a novel peptide having cell membrane permeability, and a pharmaceutical composition comprising the peptide and a hydrophilic physiologically active substance.

BACKGROUND ART

Cells are isolated from the outside by the cell membrane, which is impermeable to hydrophilic physiologically active substances such as proteins and nucleic acids. Absence of methods for delivering such hydrophilic physiologically active substances into the cell has prevented clinical use of many hydrophilic physiologically active substances whose sites of action are located in the cells.

Several techniques to deliver such cell-impermeable hydrophilic physiologically active substances have been reported. The most popular method is one which gives hydrophobicity to a hydrophilic physiologically active substance using a lipid, and, by this, permeability through the cell membrane can be increased. Further, a technique wherein a peptide ligand is used to increase the permeability has also been reported.

A peptide ligand having a property which allows its transfer from the outside of the cell into the cell without destroying the cell membrane is called a cell-penetrating peptide. Examples of well-known cell-penetrating peptides include oligoarginines, wherein arginines are linked to each other; Tat (Patent Document 1), which is derived from HIV-1 virus; and penetratin (Patent Document 2), which is a peptide derived from *Drosophila*. In addition to these, various cell-penetrating peptides, such as those characterized by simple basicity, those characterized by amphipathicity of the primary structure or the secondary structure of the peptide, and those having a mechanism which has not been clarified, have also been reported. In addition to the permeability of the peptide itself into the cell, its use for delivering into the cell a hydrophilic physiologically active substance such as a gene to which the peptides is linked as a vehicle has been extensively studied. However, although these peptides have been successful as reagents for research, only a small number of peptides can be used for clinical application. Therefore, the peptides have been studied in various ways, and, in each use, sequences with which the peptides can be more efficiently transferred into cells are being searched.

A part of cell-penetrating peptides are reported to be capable of promoting permeation of a hydrophilic physiologically active substance through the mucosal epithelial cell layer in cases where these are orally or intranasally administered together with the hydrophilic physiologically active substance, allowing the hydrophilic physiologically active substance to pass into the general circulation with a high efficiency. It is thought that not all of the cell-penetrating peptides have the permeation-promoting capacity through mucosa, and that not only cell membrane permeability but also the intracellular dynamics, separation from the cell, and the like are involved in the permeation-promoting capacity. Thus, it is thought that only a part of the cell-penetrating peptides, which satisfy these conditions, have the ability to promote transmucosal absorption of hydrophilic physiologically active substances. However, only a small number of types of peptides are reported to have such a function. Further, the peptides for which the transmucosal absorption-promoting capacity has been reported are those with which the effect can be confirmed only in cases where they are used in the forms of conjugates with particular physiologically active substances (Patent Documents 2 and 3); and those which require, even in cases where the possibility that the peptides can be used in the forms not requiring covalent bonding with a drug is shown, large amounts of the cell-penetrating peptides in order to obtain a sufficient effect (Patent Document 4). Therefore, many problems remain to be solved before practical use of the peptides.

In recent years, in addition to low molecular hydrophobic drugs, which have been mainly used so far, hydrophilic physiologically active substances are drawing attention as candidate compounds of pharmaceuticals. Although the hydrophilic physiologically active substances have shown remarkable therapeutic effects, their poor transmucosal absorbability has limited the method of their administration almost only to injection. Therefore, development of a technology to allow absorption of hydrophilic physiologically active substances through mucosa is strongly desired for the purpose of non-injection administration of hydrophilic physiologically active substances. In particular, the absorption-promoting technique using a cell-penetrating peptide is expected to show a lower level of stimulation to mucosa compared to the absorption-promoting technique using surfactants, which has been extensively studied so far, and discovery of cell-penetrating peptides that cause efficient promotion of absorption may lead to development of a promising technique.

PRIOR ART DOCUMENTS

Patent Documents

[Patent Document 1] JP 10-33186 A
[Patent Document 2] Japanese Translated PCT Patent Application Laid-open No. 2002-530059
[Patent Document 3] WO 2004/037859
[Patent Document 4] JP 10-95738 A

DISCLOSURE OF THE INVENTION

Problems to be Solved by the Invention

The present invention aims to provide a novel cell-penetrating peptide which can allow a hydrophilic physiologically active substance to permeate into the cell.

Means for Solving the Problems

The present inventors searched for peptide sequences having cell membrane permeability, and discovered novel peptide sequences having the desired cell membrane permeability. That is, the present invention has the following constitution.

(1) A cell-penetrating peptide which is any of (A) to (D) below:

(A) a peptide having the amino acid sequence represented by SEQ ID NO:1;

(B) a peptide having an amino acid sequence which is the same as the amino acid sequence represented by SEQ ID NO:1 except that one or several basic amino acids are substituted, deleted, inserted and/or added, which peptide has cell membrane permeability;

(C) a peptide having an amino acid sequence which is the same as the amino acid sequence represented by SEQ ID NO:1 except that 1 to 5 amino acids are substituted, deleted, inserted and/or added, which peptide has cell membrane permeability;

(D) a peptide having: an amino acid sequence represented by the reverse sequence of any of (A) to (C); an amino acid sequence which is the same as the amino acid sequence represented by the reverse sequence of (A) except that one or several basic amino acids are substituted, deleted, inserted and/or added; or an amino acid sequence which is the same as the amino acid sequence represented by the reverse sequence of (A) except that 1 to 5 amino acids are substituted, deleted, inserted and/or added; which peptide has cell membrane permeability.

(2) The cell-penetrating peptide according to (1), wherein the peptide (B) has the amino acid sequence represented by any of SEQ ID NOs:2 to 4, 9 to 10 and 13.

(3) The cell-penetrating peptide according to (1) or (2), wherein the peptide (C) has the amino acid sequence represented by any of SEQ ID NOs:12 and 15 to 30.

(4) The cell-penetrating peptide according to (1) to (3), wherein the peptide (D) has the amino acid sequence represented by SEQ ID NO:5 or 14.

(5) A pharmaceutical composition comprising the cell-penetrating peptide according to any of (1) to (4) and a hydrophilic physiologically active substance.

(6) A pharmaceutical composition for oral administration, the pharmaceutical composition comprising the cell-penetrating peptide according to any of (1) to (4) and a hydrophilic physiologically active substance.

(7) A pharmaceutical composition for intranasal administration, the pharmaceutical composition comprising the cell-penetrating peptide according to any of (1) to (4) and a hydrophilic physiologically active substance, (8) The pharmaceutical composition according to any of (5) to (7), wherein the hydrophilic physiologically active substance is a peptide, protein or nucleic acid.

Effect of the Invention

By the present invention, efficient transfer of a hydrophilic physiologically active substance into cells is possible, and a novel pharmacotherapy targeting molecules in the cell is possible. Further, a hydrophilic physiologically active substance which has been able to be administered only by injection can be administered by oral administration, intranasal administration or the like, enabling a simple and patient-oriented pharmacotherapy.

BEST MODE FOR CARRYING OUT THE INVENTION

Figure 1:
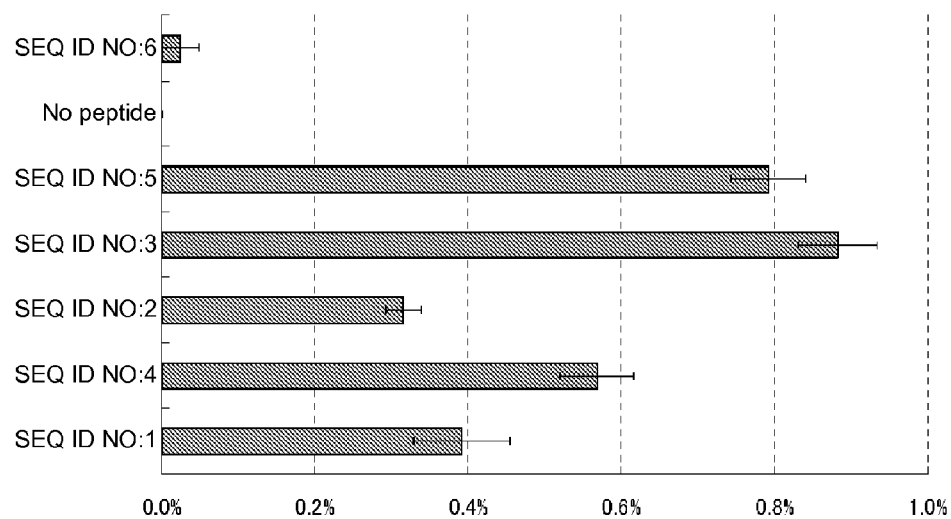
FIG. 1 is a graph showing transfer of cell-penetrating peptides into HeLa cells

The present inventors newly discovered that a peptide having the amino acid sequence shown in SEQ ID NO:1 (hereinafter referred to as the peptide of SEQ ID NO:1) or its modified peptide is a cell-penetrating peptide, thereby completing the present invention. The cell-penetrating peptides of the present invention will now be described below in detail.

The cell membrane permeability of a cell-penetrating peptide of the present invention means a property to pass through a lipid membrane separating the inside of the cell from the outside thereof. Whether or not a peptide having cell-membrane permeability can be confirmed by linking a fluorescent substance to the peptide and adding the resultant to cells, followed by observing the cells by a confocal laser microscope or the like to see if the fluorescent substance can be detected in the cells. Further, quantitative confirmation of permeability into cells can be carried out by incorporating the fluorescent substance-linked peptide into the cells and homogenizing the cells, followed by measuring the fluorescence intensity of the homogenate using a spectrophotometer. In the present specification, in cases where the amount of permeation of a fluorescent substance (e.g., fluorescein)-linked peptide into cells is not less than 3 times higher than the amount of permeation of a fluorescent substance-linked cell membrane non-permeable peptide having the amino acid sequence represented by SEQ ID NO:6 into the cells, the former peptide is judged to be a cell-penetrating peptide.

Further, the cell-penetrating peptides of the present invention have a property to give cell membrane permeability to hydrophilic physiologically active substances. In the present specification, when the efficiency of permeation of a fluorescently labeled hydrophilic physiologically active substance into cells is not less than 3 times higher in cases where the fluorescently labeled hydrophilic physiologically active substance is linked to or mixed with a peptide and brought into contact with cells than in cases where the fluorescently labeled hydrophilic physiologically active substance alone is brought into contact with cells, the peptide is judged to have a property to give cell membrane permeability to the hydrophilic physiologically active substance.

Further, the cell-penetrating peptides of the present invention have a property to give transmucosal absorbability (preferably intestinal absorbability or intranasal absorbability) to hydrophilic physiologically active substances. More particularly, even in cases where a hydrophilic physiologically active substance is hardly absorbed by itself into the living body through mucosa, its transmucosal absorption (preferably intestinal absorption or intranasal absorption) is promoted by bringing the hydrophilic physiologically active substance linked to or mixed with a cell-penetrating peptide into contact with the mucosal tissue (preferably intestinal tissue or intranasal tissue).

The peptide having the amino acid sequence shown in SEQ ID NO:1 is a novel peptide discovered by screening of cell-penetrating peptides. The type of the cell through which the peptide passes through is not restricted and may be either a prokaryotic cell or eukaryotic cell, and the peptide can preferably pass through the cell membrane of a eukaryotic cell, preferably mammalian cell, still more preferably through the mucosal cell membrane of a mammal. The peptide per se has cell membrane permeability, and moreover, by covalently binding the peptide to a hydrophilic physiologically active substance, cell membrane permeability can be given to the hydrophilic physiologically active substance. Preferably, the peptide can give cell membrane permeability to a hydrophilic physiologically active substance even in cases where the peptide and the hydrophilic physiologically active substance exist independently from each other in a composition.

Further, a modified peptide having an amino acid sequence which is the same as the amino acid sequence represented by SEQ ID NO:1 except that one or several basic amino acids are substituted, deleted, inserted and/or added is also a cell-penetrating peptide of the present invention as long as the modified peptide has cell membrane permeability. Here, the basic amino acid means any of the amino acids arginine, lysine and histidine. The number of the substituted, deleted, inserted and/or added basic amino acid(s) is preferably 1 to 7, more preferably 1 to 5, still more preferably 1 to 3, especially preferably 1. In the amino acid sequence which has been mutated by the substitution, deletion and/or insertion, a sequence of not less than 3 continuous amino acids in the original amino acid sequence is preferably conserved, and a sequence of not less than 5 continuous amino acids in the original amino acid sequence is more preferably conserved. Further, in the case of a modified peptide produced by substituting a basic amino acid(s) of the amino acid sequence represented by SEQ ID NO:1 with another/other basic amino acid(s), the modification is most acceptable since substitution with another amino acid having the same property is not likely to change the overall property of the peptide. Preferred examples of the peptide having an amino acid sequence which is the same as the amino acid sequence represented by SEQ ID NO:1 except that one or several basic amino acids are deleted, substituted and/or added, which peptide has cell membrane permeability, include peptides having the amino acid sequences represented by any of SEQ ID NOs:2 to 4, 9 to 10 and 13.

Further, a modified peptide having an amino acid sequence which is the same as the amino acid sequence represented by SEQ ID NO:1 except that 1 to 5, preferably 1 to 3, more preferably 1 to 2, still more preferably 1 amino acid(s), which is/are not limited to a basic amino acid(s), is/are substituted, deleted, inserted and/or added is also a cell-penetrating peptide of the present invention as long as the modified peptide has cell membrane permeability. In the amino acid sequence produced by substitution, deletion, insertion and/or addition of an amino acid(s) in SEQ ID NO:1, a sequence of not less than 3 continuous amino acids in the original amino acid sequence is preferably conserved, and a sequence of not less than 5 continuous amino acids in the original amino acid sequence is more preferably conserved. Further, for example, in cases where a basic amino acid(s) in the amino acid sequence represented by SEQ ID NO:1 is/are substituted with another/other basic amino acid(s); in cases where a hydrophilic amino acid(s) in the amino acid sequence represented by SEQ ID NO:1 is/are substituted with another/other hydrophilic amino acid(s); and in cases where a hydrophobic amino acid(s) in the amino acid sequence represented by SEQ ID NO:1 is/are substituted with another/other hydrophobic amino acid(s); the modification is most acceptable since substitution with an amino acid having the same property is not likely to change the overall property of the peptide. Preferred examples of the peptide having an amino acid sequence which is the same as the amino acid sequence represented by SEQ ID NO:1 except that 1 to 5 amino acids, which is/are not limited to a basic amino acid(s), are substituted, deleted, inserted and/or added, which peptide has cell membrane permeability, include peptides having the amino acid sequences represented by any of SEQ ID NOs:12 and 15 to 30.

Further, a peptide having the amino acid sequence represented by the reverse sequence of the peptide having the amino acid sequence represented by SEQ ID NO:1; a peptide having an amino acid sequence represented by the reverse sequence of an amino acid sequence which is the same as the amino acid sequence represented by SEQ ID NO:1 except that one or several basic amino acids are substituted, deleted, inserted and/or added; a peptide having an amino acid sequence which is the same as the reverse sequence of the amino acid sequence represented by SEQ ID NO:1 except that one or several basic amino acids are substituted, deleted, inserted and/or added; a peptide having an amino acid sequence represented by the reverse sequence of an amino acid sequence which is the same as the amino acid sequence represented by SEQ ID NO:1 except that 1 to 5 amino acids, which are not limited to basic amino acids, are substituted, deleted, inserted and/or added; and a peptide having an amino acid sequence which is the same as the reverse sequence of the amino acid sequence represented by SEQ ID NO:1 except that 1 to 5 amino acids, which are not limited to basic amino acids, are substituted, deleted, inserted and/or added; are also cell-penetrating peptides of the present invention as long as these have cell membrane permeability. Here, the peptide having the reverse sequence means that the sequence of the constituting amino acids is reversed, and, for example, when the sequence of the amino acids from the N-terminus to the C-terminus is arginine, glutamine, isoleucine and lysine, the reverse peptide thereof means the peptide whose sequence of amino acids from the N-terminus to the C-terminus is lysine, isoleucine, glutamine and arginine. Particular examples thereof include a peptide having the amino acid sequence represented by SEQ ID NO:5 or 14, which has the amino acid sequence represented by the reverse sequence of the peptide having the amino acid sequence represented by SEQ ID NO:1 and has cell membrane permeability.

As the amino acids constituting the cell-penetrating peptides of the present invention, amino acids having the configuration of L-body, which are naturally occurring amino acids, as well as non-naturally occurring amino acids such as derivatives produced by partial modification of the structures of naturally occurring amino acids may be used. For example, since amino acids having the configuration of D-body are not likely to be degraded by proteases and hence can be effectively used, a part of the amino acid sequence of the peptide may have the configuration of D-body.

The amino acids constituting the cell-penetrating peptides of the present invention are not restricted as long as they are molecules having a carboxyl group and an amino group irrespective of whether these naturally exist, and may also be amino acids modified by post-translational modification normally seen in the living body, such as hydroxylation, phosphorylation or glycosylation. The amino acid sequence is preferably composed of naturally-occurring amino acids normally existing in mammalian cells and/or optical isomers thereof, and examples of the amino acid sequence include those composed of arginine (Arg), lysine (Lys), aspartic acid (Asp), asparagine (Asn), glutamic acid (Glu), glutamine (Gln), histidine (His), proline (Pro), tyrosine (Tyr), tryptophan (Trp), serine (Ser), threonine (Thr), glycine (Gly), alanine (Ala), methionine (Met), cysteine (Cys), phenylalanine (Phe), leucine (Leu), valine (Val), isoleucine (Ile) and/or the like.

The cell-penetrating peptides of the present invention may be modified as appropriate by methods known to those skilled in the art, and more particularly, these may be derivatives chemically modified by polyethylene glycolation (PEGylation), acetylation of the N-terminus, amidation of the C-terminus, and/or the like. It should be noted that, in cases where a cell-penetrating peptide of the present invention is used for the later-mentioned pharmaceutical composition, the peptide is preferably not modified. Further, the cell-penetrating peptides of the present invention may be either linear or circular.

The cell-penetrating peptides of the present invention may be used in combination with other known cell-penetrating peptides. Further, the cell-penetrating peptides of the present invention may be used in the forms of fusion peptides or fusion proteins prepared by fusing the peptides with other peptides or proteins by the later-mentioned method, as long as the cell membrane permeability is maintained.

The cell-penetrating peptides of the present invention may be produced by common chemical synthesis methods. Examples of the production method include the peptide synthesis methods by the commonly used liquid phase method or solid phase method. Examples of such peptide synthesis methods include the stepwise elongation method, wherein each amino acid is successively bound to elongate a chain, and the fragment condensation method, wherein fragments composed of several amino acids are preliminarily synthesized followed by subjecting the respective fragments to the coupling reaction. Synthesis of the cell-penetrating peptides of the present invention may be carried out by either of these methods.

The condensation method employed for the above peptide synthesis may also be carried out according to various known methods. Particular examples thereof include the azide method, mixed anhydride method, DCC method, active ester method, oxidation-reduction method, DPPA (diphenylphosphorylazide) method, DCC+additives (e.g., 1-hydroxybenzotriazole, N-hydroxysuccinimide and N-hydroxy-5-norbornene-2,3-dicarboxyimide) and Woodward method. The solvent that can be used for each of these methods may be appropriately selected from commonly used ones which are well known to be used for such types of peptide condensation reactions. Examples of the solvent include dimethylformamide (DMF), dimethylsulfoxide (DMSO), hexamethylphosphoramide, dioxane, tetrahydrofuran (THF) and ethyl acetate, and mixed solvents thereof.

In the above-described peptide synthesis reactions, carboxyl groups of amino acids or peptides which are not involved in the reactions may be generally protected by esterification to form a lower-alkyl ester such as a methyl ester, ethyl ester or tert-butyl ester; or an aralkyl ester such as a benzyl ester, p-methoxybenzyl ester or p-nitrobenzyl ester. Further, hydroxyl groups of amino acids having functional groups in their side chains, for example, the hydroxyl group of Tyr, may be protected by an acetyl group, benzyl group, benzyloxycarbonyl group, tert-butyl group or the like, but such protection is not necessarily required. Further, the guanidino group of Arg may be protected with an appropriate protecting group such as a nitro group, tosyl group, 2-methoxybenzenesulfonyl group, methylene-2-sulfonyl group, benzyloxycarbonyl group, isobornyloxycarbonyl group or adamantyloxycarbonyl group. Deprotection reactions for these protecting groups in the amino acids, the peptides, and the finally obtained peptides of the present invention may also be carried out according to conventional methods such as the catalytic reduction method and methods using liquid ammonia/sodium, hydrogen fluoride, hydrogen bromide, hydrogen chloride, trifluoroacetic acid, acetic acid, formic acid and methanesulfonic acid.

Alternatively, the cell-penetrating peptides of the present invention may be prepared by conventional methods using genetic engineering techniques. The thus obtained cell-penetrating peptides of the present invention may be purified as appropriate according to methods commonly used in the field of peptide chemistry, such as those using ion-exchange resins, partition chromatography, gel chromatography, affinity chromatography, high performance liquid chromatography (HPLC) and the countercurrent distribution method.

Alternatively, the cell-penetrating peptides of the present invention may be used in the forms of nucleic acids encoding the peptides. Particular examples of the nucleic acids include, but are not limited to, plasmid vectors, virus vectors, phagemids and transposons which contain recombinant nucleic acids encoding fusion proteins with the peptides of the present invention and which allow expression of these peptides. Further, the recombinant nucleic acids are preferably used for, for example, industrial production of a cell-penetrating peptide of the present invention, or a fusion protein with a cell-penetrating peptide of the present invention; introduction of an expression vector encoding a cell-penetrating peptide of the present invention into living body-derived cells removed from the body; and administration of a cell-penetrating peptide of the present invention to the body to make cells in the body express the cell-penetrating peptide of the present invention or a fusion protein therewith. In particular, the recombinant nucleic acids are preferably used for methods of in vitro production of cell-penetrating peptides of the present invention or fusion proteins with cell-penetrating peptides of the present invention.

The recombinant nucleic acid means DNA or RNA which was artificially prepared. Examples of the recombinant nucleic acid include those synthesized by linking nucleic acids such as adenine, cytosine, guanine, thymine and/or uracil with each other; those prepared by cleaving out a part of DNA or RNA contained in an organism and modifying it by removal of a part of its bases, linking it with other bases, and/or the like; and those prepared by replicating these recombinant nucleic acids.

Further, the present invention relates to a pharmaceutical composition containing a cell-penetrating peptide and a hydrophilic physiologically active substance, and a method of administration of a hydrophilic physiologically active substance to the living body by combined use of a cell-penetrating peptide of the present invention and the hydrophilic physiologically active substance.

Because of not only the fact that the cell-penetrating peptides of the present invention themselves have cell membrane permeability, but also the fact that the peptides can give cell membrane permeability to hydrophilic physiologically active substances, in vivo delivery of a hydrophilic physiologically active substance through the cell membrane is possible by blending of a cell-penetrating peptide of the present invention in a pharmaceutical composition comprising as an effective component the hydrophilic physiologically active substance or by administration of the hydrophilic physiologically active substance and a cell-penetrating peptide of the present invention in combination. More particularly, since a cell-penetrating peptide of the present invention can not only preferably pass through the mucosal cell membrane but also give transmucosal absorbability (preferably intestinal absorbability or intranasal absorbability) to a hydrophilic physiologically active substance, in vivo delivery of the hydrophilic physiologically active substance through mucosa is possible. The transmucosal absorption of a hydrophilic physiologically active substance means that a hydrophilic physiologically active substance administered to mucosa passes into the blood through a mucosal layer, and its result can be confirmed by increase in the blood level of the hydrophilic physiologically active substance or expression of the pharmacological activity. The blood level of a hydrophilic physiologically active substance can be measured by a method normally used by those skilled in the art, such as an immunoassay. The pharmacological activity can be measured using as an index, in the case of an enzyme, its enzymatic activity, or, in the case of a substance that acts on a receptor in the cell, an ability to change a function of the target cell or the production amount of a marker substance. For example, the pharmacological activity of insulin can be measured using as an index the blood glucose level of the animal to which insulin was administered.

The cell-penetrating peptide which gives cell membrane permeability, preferably transmucosal absorbability, to a hydrophilic physiologically active substance is not restricted as long as the peptide is the above-mentioned cell-penetrating peptide of the present invention, and particular examples thereof include a peptide having the amino acid sequence represented by SEQ ID NO:1 and a modified peptide produced by substituting, deleting, inserting and/or adding 1 to 7, preferably 1 to 5, more preferably 1 to 2 basic amino acids in the amino acid sequence represented by SEQ ID NO:1, which modified peptide has cell membrane permeability. In particular, examples of a cell-penetrating peptide of the present invention which gives intranasal absorbability to a hydrophilic physiologically active substance and is preferably used for a pharmaceutical composition for intranasal administration include a peptide having the amino acid sequence represented by SEQ ID NO:1 and a modified peptide produced by substituting, deleting, inserting and/or adding 1 or 2 basic amino acid(s) in the amino acid sequence represented by SEQ ID NO:1, which modified peptide has cell membrane permeability. Particular examples of a peptide which is a cell-penetrating peptide of the present invention and gives intranasal absorbability to a hydrophilic physiologically active substance; which peptide is a modified peptide produced by substituting, deleting, inserting and/or adding 1 or 2 basic amino acid(s) in the amino acid sequence represented by SEQ ID NO:1; which peptide has cell membrane permeability; are shown in Table 1. In the modified peptide, substitution of a basic amino acid(s) in the amino acid sequence represented by SEQ ID NO:1 with another/other basic amino acid(s) is most acceptable since substitution with a peptide having the same property is not likely to change the overall property of the peptide.

TABLE 1

| SEQ ID NO: 1  | R W F K I Q M Q I R R W K N K K |
|---|---|
| SEQ ID NO: 31 | K W F K I Q M Q I R R W K N K K |
| SEQ ID NO: 32 | R W F R I Q M Q I R R W K N K K |
| SEQ ID NO: 33 | R W F K I Q M Q I K R W K N K K |
| SEQ ID NO: 34 | R W F K I Q M Q I R K W K N K K |
| SEQ ID NO: 35 | R W F K I Q M Q I R R W R N K K |
| SEQ ID NO: 36 | R W F K I Q M Q I R R W K N R K |
| SEQ ID NO: 37 | R W F K I Q M Q I R R W K N K R |
| SEQ ID NO: 10 | K W F K I Q M Q I R R W K N K R |
| SEQ ID NO: 9  | K W F K I Q M Q I R R W K N R K |
| SEQ ID NO: 38 | K W F K I Q M Q I R R W R N K K |
| SEQ ID NO: 39 | K W F K I Q M Q I R K W K N K K |
| SEQ ID NO: 40 | K W F K I Q M Q I K R W K N K K |
| SEQ ID NO: 41 | K W F R I Q M Q I R R W K N K K |
| SEQ ID NO: 42 | R W F R I Q M Q I R R W K N K R |
| SEQ ID NO: 43 | R W F R I Q M Q I R R W K N R K |
| SEQ ID NO: 44 | R W F R I Q M Q I R R W R N K K |
| SEQ ID NO: 45 | R W F R I Q M Q I R K W K N K K |
| SEQ ID NO: 46 | R W F R I Q M Q I K R W K N K K |
| SEQ ID NO: 47 | R W F K I Q M Q I K R W K N K R |
| SEQ ID NO: 48 | R W F K I Q M Q I K R W K N R K |
| SEQ ID NO: 49 | R W F K I Q M Q I K R W R N K K |
| SEQ ID NO: 50 | R W F K I Q M Q I K K W K N K K |
| SEQ ID NO: 51 | R W F K I Q M Q I R K W K N K R |
| SEQ ID NO: 52 | R W F K I Q M Q I R K W K N R K |
| SEQ ID NO: 53 | R W F K I Q M Q I R K W R N K K |
| SEQ ID NO: 54 | R W F K I Q M Q I R R W R N K R |
| SEQ ID NO: 55 | R W F K I Q M Q I R R W R N R K |
| SEQ ID NO: 56 | R W F K I Q M Q I R R W K N R R |

Preferred examples of a peptide having an amino acid sequence which is the same as the amino acid sequence represented by SEQ ID NO:1 except that one or several basic amino acids are deleted, substituted and/or added, which peptide gives transmucosal absorbability to a hydrophilic physiologically active substance, include a peptide having the amino acid sequence represented by any of SEQ ID NO:4, SEQ ID NO:9 and SEQ ID NO:10, and, in particular, preferred examples of a peptide which gives intranasal absorbability to a hydrophilic physiologically active substance include a peptide having the amino acid sequence represented by SEQ ID NO:9 or 10.

Further, a cell-penetrating peptide of the present invention which is a modified peptide represented by a sequence which is the same as the amino acid sequence represented by SEQ ID NO:1 except that 1 to 5, preferably 1 to 3, more preferably 1 or 2, still more preferably 1 amino acid(s) not limited to a basic amino acid(s) is/are substituted, deleted, inserted and/or added, which modified peptide enables transmucosal absorption of a hydrophilic physiologically active substance, may also be used for a pharmaceutical composition of the present invention. In the sequence which has been mutated by the substitution, deletion and/or insertion, a sequence of not less than 3 continuous amino acids in the original amino acid sequence is preferably conserved, and a sequence of not less than 5 continuous amino acids in the original amino acid sequence is more preferably conserved. Further, substitution with another peptide having the same property, such as substitution of a basic amino acid(s) with another/other basic amino acid(s), substitution of a hydrophilic amino acid(s) with another/other hydrophilic amino acid(s), and/or substitution of a hydrophobic amino acid(s) with another/other hydrophobic amino acid(s) in the amino acid sequence represented by SEQ ID NO:1, is the most acceptable change since the overall property of the peptide is not likely to change in this case.

Further, a cell-penetrating peptide of the present invention which enables transmucosal absorption of a hydrophilic physiologically active substance, which cell-penetrating peptide is a peptide having the amino acid sequence represented by the reverse sequence of the peptide having the amino acid sequence represented by SEQ ID NO:1; a peptide having an amino acid sequence represented by the reverse sequence of an amino acid sequence which is the same as the amino acid sequence represented by SEQ ID NO:1 except that one or several basic amino acids are substituted, deleted, inserted and/or added; a peptide having an amino acid sequence which is the same as the reverse sequence of the amino acid sequence represented by SEQ ID NO:1 except that one or several basic amino acids are substituted, deleted, inserted and/or added; a peptide having an amino acid sequence represented by the reverse sequence of an amino acid sequence which is the same as the amino acid sequence represented by SEQ ID NO:1 except that 1 to 5 amino acids, which are not limited to basic amino acids, are substituted, deleted, inserted and/or added; or a peptide having an amino acid sequence which is the same as the reverse sequence of the amino acid sequence represented by SEQ ID NO:1 except that 1 to 5 amino acids, which are not limited to basic amino acids, are substituted, deleted, inserted and/or added; may also be used for a pharmaceutical composition of the present invention, The hydrophilic physiologically active substance means a physiologically active substance having a property of hydrophilicity. The hydrophilicity means that the solubility in water is high, and, in the present specification, a substance is defined to be hydrophilic when not less than 1 μg of the substance is soluble to 1 ml of water. The physiologically active substance means any substance that acts on a living body to cause change in the living body, and examples thereof include proteins which are bound to receptors in specific cells, and enzymes having affinities to substances in a living body. Further, the physiologically active substance may also be a substance which does not directly react with a substance in a living body, and, for example, it may also be a substance which can be administered to a living body for a medical purpose, such as dextran employed for increasing blood as an alternative to plasma. The physiologically active substance is preferably a peptide, protein or nucleic acid, more preferably a peptide or protein, which is poorly permeable through a biological barrier such as the cell membrane or a transmucosal constituent cell layer. Further, glycoproteins wherein sugar chains are bound to these proteins which are hydrophilic physiologically active substances, and protein derivatives produced by chemical modification such as polyethylene glycolation (PEGylation) are also preferably used as the hydrophilic physiologically active substances.

The molecular weight of the hydrophilic physiologically active substance is not restricted, but in cases where the molecular weight is too high, passage of the substance through the cell membrane is sometimes prevented, so that the molecular weight is preferably not more than 500,000, more preferably not more than 30,000.

Particular preferred examples of the hydrophilic physiologically active substance include parathyroid hormone (PTH), calcitonin, insulin, angiotensin, glucagon, glucagon-like peptide (GLP-1), exendin-4, gastrin, growth hormone, prolactin (luteotropic hormone), gonadotropin (gonadotropic hormone), cytotropic hormone, adrenocorticotropic hormone, melanocyte-stimulating hormone, vasopressin, oxytocin, protirelin, luteinizing hormone (LH), corticotropin, somatropin, thyrotropin (thyroid-stimulating hormone), somatostatin (growth hormone-stimulating factor), hypothalamic hormone (GnRH), G-CSF, erythropoietin, HGF, EGF, VEGF, angiopoietin, interferon-α, interferon-β, interferon-γ, interleukins, superoxide dismutase (SOD), urokinase, lysozyme and vaccines, and the hydrophilic physiologically active substance is more preferably insulin, calcitonin, parathyroid hormone, growth hormone, interferon, interleukin, G-CSF, glucagon-like peptide (GLP-1) or exendin-4.

In one preferred mode of the present invention, the cell-penetrating peptide and the hydrophilic physiologically active substance form a conjugate. The "conjugate" herein means a state wherein not less than 2 substances can move at the same time, and the conjugate also includes substances bound to each other by covalent bonding, substances electrostatically bound to each other by ionic bonding, and substances which are not bound to each other but have spatial structures by which one of these can limit movement of the other(s), enabling the substances to move together. For example, a particle such as a micelle, liposome or macromolecule whose surface is modified with a peptide of the present invention and which encloses a biologically active drug therein can be said to be forming a "conjugate". Examples of the conjugate include one wherein a peptide of the present invention and a hydrophilic physiologically active substance arc covalently bound to each other. Examples of such a conjugate include a pharmaceutical composition wherein an amino group or carboxyl group, or the thiol group of cysteine, in a protein which is a hydrophilic physiologically active substance and a cell-penetrating peptide of the present invention are covalently bound to each other.

In cases where a cell-penetrating peptide and a protein which is a hydrophilic physiologically active substance are made into a conjugate, the conjugate may be prepared as a fusion protein. The site of addition of the cell-penetrating peptide of the present invention is not restricted, and preferably, the peptide having cell membrane permeability is presented on the outside of the protein and does not largely affect the activity and the function of the protein after the fusion. The cell-penetrating peptide is preferably fused to the N-terminus or C-terminus. The type of the protein to be fused is not restricted, but, since a drug is prevented from passing through the cell membrane in cases where its molecular weight it too high, the molecular weight of the protein is preferably not more than 500,000, more preferably not more than 30,000.

The fusion protein with a cell-penetrating peptide may be produced by a common chemical synthesis method. Examples of the method include a method wherein a cell-penetrating peptide of the present invention and insulin are mixed together and bound to each other by addition of a condensing agent, and a method using a peptide synthesizer (e.g., Applied Biosystems Medel 433). Further, the fusion protein may be produced based on the nucleic acid sequence information using a genetic engineering technique according to a conventional method. Examples of the method include a method wherein a nucleic acid sequence encoding a cell-penetrating peptide of the present invention and a protein to be fused is incorporated into a gene expression vector having a promoter for protein expression, followed by producing a fusion protein.

Further, in another preferred mode of the present invention, the cell-penetrating peptide and the hydrophilic physiologically active substance are used in a state where these are not covalently linked to each other. Even in cases where the cell-penetrating peptide and the hydrophilic physiologically active substance are not forming a conjugate by covalent bonding when a pharmaceutical composition of the present invention is administered, a desired effect can be obtained by a process wherein the cell-penetrating peptide and the hydrophilic physiologically active substance are mixed with each other after their administration and then the peptide and the hydrophilic physiologically active substance form a conjugate by ionic bonding, hydrophobic action and/or charge action. Since, in such cases, direct modification of the hydrophilic physiologically active substance is not necessary, the bioactivity originally retained by the hydrophilic physiologically active substance is not affected, which is preferred.

In the present invention, the mucosa through which transmucosal absorption of the hydrophilic physiologically active substance is possible is not limited, and examples thereof include mucosa of the eye, nasal cavity, hypoglottis, lung, oral cavity, skin, vagina and intestine. The mucosa is preferably mucosa of the nasal cavity or intestine. Further, the administration method for transmucosal absorption of the hydrophilic physiologically active substance by the present invention is not limited, and examples of the administration method include oral, nasal, rectal and percutaneous administration and administration by injection. The administration method is preferably oral, nasal or rectal administration.

In the present invention, the dose and the number of doses for administration of the hydrophilic physiologically active substance and the cell-penetrating peptide to a living body may be appropriately selected depending on the hydrophilic physiologically active substance, dosage form, age of the patient, body weight and severity of symptoms, and usually, they are administered at a dose of 0.01 to 50 mg, preferably 0.1 to 20 mg per adult per day in terms of the content of the hydrophilic physiologically active substance. The blend ratio of the cell-penetrating peptide and the hydrophilic physiologically active substance is not restricted, and the ratio is preferably determined depending on the type of the hydrophilic physiologically active substance blended and the mode of blending of the cell-penetrating peptide and the hydrophilic physiologically active substance. In order to give a sufficient action to the hydrophilic physiologically active substance, the cell-penetrating peptide is used, in any mode of blending, in an amount preferably not less than 1 time larger, more preferably not less than 2 times larger than the molar amount of the hydrophilic physiologically active substance which is to be allowed to act. This means that, in cases where the cell-penetrating peptide and the hydrophilic physiologically active substance are forming a conjugate by covalent bonding, not less than 1 cell-penetrating peptide is bound to each hydrophilic physiologically active substance, and, in cases where these are independently used, not less than 1 mole of the cell-penetrating peptide is contained with respect to 1 mole of the hydrophilic physiologically active substance used.

In the present invention, the mode of administration of the hydrophilic physiologically active substance and the cell-penetrating peptide to an animal (including human) is not particularly restricted. For example, these may be administered as they are in the dry state or in the form of a solution, or may be filled in a capsule together with a vehicle followed by administration of the capsule. Further, those in the dry state may be once dissolved or dispersed in water and then administered.

Examples of the form of the pharmaceutical composition of the present invention include powder forms composed of the cell-penetrating peptide and the hydrophilic physiologically active substance as well as pharmaceutically acceptable additives; liquid forms composed of a mixture with a medium, such as water, and a pharmaceutically acceptable base other than the medium, and the like; and solid or semi-solid forms composed of a combination with a pharmaceutically acceptable base. Examples of the base include various organic and inorganic substances commonly used as formulation materials, such as vehicles, lubricants, binders, disintegrators, solvents, solubilizers, suspending agents, isotonic agents, buffering agents, soothing agents and absorption enhancers. Particular examples thereof include water, pharmaceutically acceptable organic solvents, collagen, polyvinyl alcohol, polyvinylpyrrolidone, carboxyvinyl polymers, sodium carboxymethylcellulose, sodium polyacrylate, sodium alginate, water-soluble dextran, sodium carboxymethyl starch, pectin, methyl cellulose, ethyl cellulose, xanthan gum, gum arabic, casein, gelatin, agar, diglycerol, propylene glycol, polyethylene glycol, vaseline, paraffin, stearyl alcohol, stearic acid, human serum albumin (HSA), mannitol, sorbitol, lactose, and surfactants acceptable as pharmaceutical additives.

Further, the pharmaceutical composition of the present invention may be preferably used in combination not only with simple additives but also with advanced delivery techniques. For example, for the purpose of delivering a pharmaceutical composition of the present invention to the intestinal tract by oral administration, it is preferred to encapsulate the pharmaceutical composition in an enteric capsule or in mucoadhesive hydroxypropylcellulose or Smart Hydrogel poly(methacrylic acid) grafted with poly(ethylene glycol) P(MAA-g-EG), or the like, in view of avoiding degradation of the peptide and the drug by digestive enzymes.

EXAMPLES

Example 1

Evaluation of Peptide Permeability into Cells

<Method>

In DMEM medium supplemented with 10% FBS, 0.2 ml of HeLa cells were plated on a 96-well glass bottom plate, and the cells were cultured at 37° C. for 48 to 72 hours to allow the cells to adhere to the bottom surface. After 3 times of washing with 200 µl of PBS, 50 µl of DMEM medium containing each of the peptides of SEQ ID NOs:1 to 6 labeled with fluorescein at the amino terminus (contract synthesis by Sigma-Genosys) at a final concentration of 5 µM and FBS at a final concentration of 10% was added to each well. The plate was incubated in a CO$_2$ incubator for 3 hours and then washed 3 times with DMEM medium supplemented with 10% FBS, followed by addition of 50 μl of a lysis solution (10 mM Tris-HCl, 5 mM EDTA, 100 mM NaCl, 1% SDS, 100 μg/ml proteinase K) and 1 hour of incubation at room temperature, to decompose the cells and the peptides incorporated into the cells. The whole lysis solution was recovered, and the amount of fluorescein incorporated into the cells was measured using a fluorescence intensity measuring apparatus (HORIBA FLUOROMAX-3) at an excitation wavelength of 494 nm and a fluorescence wavelength of 512 nm.

<Results>

The amount of fluorescein incorporated into the cells with respect to the amount of fluorescein added to each well is shown in FIG. 1. For each value, the average value and the standard error obtained by 3 times of evaluation are shown. In contrast to the random peptide of SEQ ID NO:6, which was hardly incorporated into the cells and hence not a cell-penetrating peptide, the fluorescein-labeled peptides of SEQ ID NOs:1 to 5, which are peptides of the present invention, were incorporated into the cells with not less than 10 times higher efficiencies than the random peptide of SEQ ID NO:6.

Example 2

Evaluation of Promotion of Insulin Transfer into Cells

<Method>

In DMEM medium supplemented with 10% FBS, 0.2 ml of HeLa cells were plated on a 96-well glass bottom plate, and the cells were cultured at 37° C. for 48 to 72 hours to allow the cells to adhere to the bottom surface. After 3 times of washing with 200 μl of PBS, 50 μl of DMEM medium containing each of the peptides of SEQ ID NOs:1 to 6 labeled with fluorescein at the amino terminus (contract synthesis by Sigma-Genosys) at a final concentration of 5 rhodamine-labeled human insulin at a final concentration of 100 μg/ml and 10% FBS was added to each well. The plate was incubated in a CO$_2$ incubator for 3 hours and then washed 3 times with DMEM medium supplemented with 10% FBS, followed by addition of 50 μl of a lysis solution (10 mM Tris-HCl, 5 mM EDTA, 100 mM NaCl, 1% SDS, 100 μg/ml proteinase K) and 1 hour of incubation at room temperature, to decompose the cells and the rhodamine-labeled insulin incorporated into the cells. The whole lysis solution was recovered, and the amount of the rhodamine-labeled insulin incorporated into the cells was measured using a fluorescence intensity measuring apparatus at an excitation wavelength of 555 nm and a fluorescence wavelength of 580 nm.

Further, in the same manner, a solution containing rhodamine-labeled human insulin and each of the peptides of SEQ ID NOs:1 to 6 was added to HeLa cells and the resultant was the incubated, followed by 3 times of washing with 300 μl of DMEM medium supplemented with 10% FBS, 3 hours of fixation with 4% paraformaldehyde solution and 3 times of washing with 300 μl of PBS. Thereafter, the cells were incubated in 5% DiD'Oil solution (Molecular probes, Inc.) overnight, and localization of the rhodamine-labeled insulin was observed using a confocal laser microscope (FV-1000, Olympus Corporation).

The rhodamine-labeled insulin was prepared by the following method. In 0.5 ml of 0.1 N hydrochloric acid, 20 mg of human insulin was dissolved, and 3 ml of PBS and 0.5 ml of 0.1 N sodium hydroxide were then added thereto to neutralize the solution. The resulting solution was subjected to solution exchange using a desalting column (PD-10 column), to obtain 5 ml of 50 mM NaHCO$_3$ solution (insulin concentration, 4 mg/ml). To the resulting solution, 4 mg of NHS-rhodamine (Pierce) dissolved in 0.5 ml of DMSO was added, and the reaction was allowed to proceed at room temperature overnight. To the reaction solution, 0.5 ml of 1 M Tris-HCl (pH 8) was added, and the resulting mixture was further allowed to react at room temperature for 30 minutes, followed by desalting against water using a PD-10 column and adding water to obtain a solution in a final volume of 10 ml (2 mg/ml in terms of the insulin concentration).

<Results>

Figure 2:
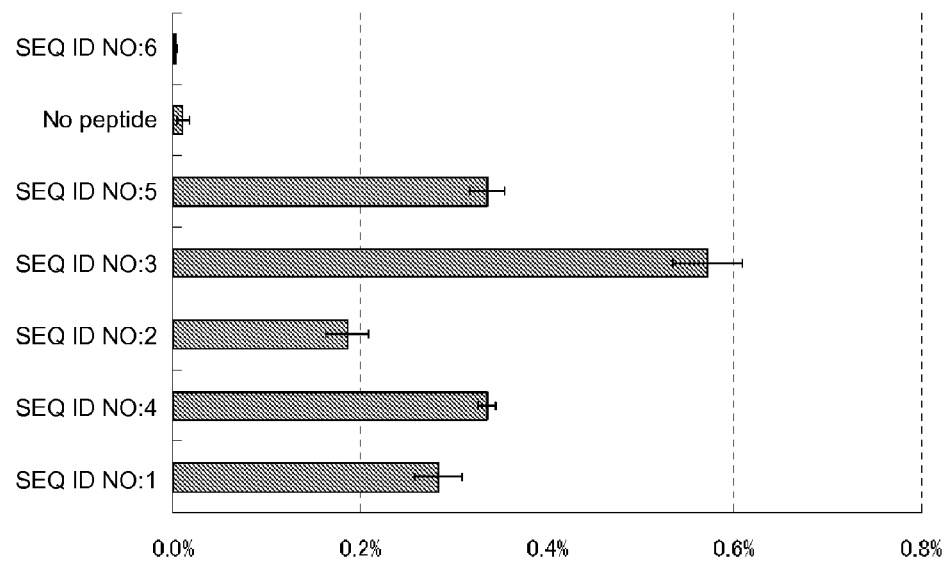
FIG. 2 is a graph showing promotion of insulin transfer into HeLa cells by cell-penetrating peptides.

The amount of rhodamine-labeled insulin incorporated into the cells with respect to the amount of rhodamine-labeled insulin added to each well is shown in FIG. 2. Each value is represented as the average value and the standard error obtained by 3 times of evaluation. Although addition of the rhodamine-labeled insulin alone and addition of the rhodamine-labeled insulin together with the peptide having the random sequence shown in SEQ ID NO:6 to the cells resulted in almost no incorporation of the rhodamine-labeled insulin into the cells, addition of the rhodamine-labeled insulin together with the peptides of SEQ ID NOs:1 to 5, which are peptides of the present invention, resulted in incorporation of the rhodamine-labeled insulin into the cells with not less than 50 times higher efficiencies than the random peptide of SEQ ID NO:6.

Figure 12:
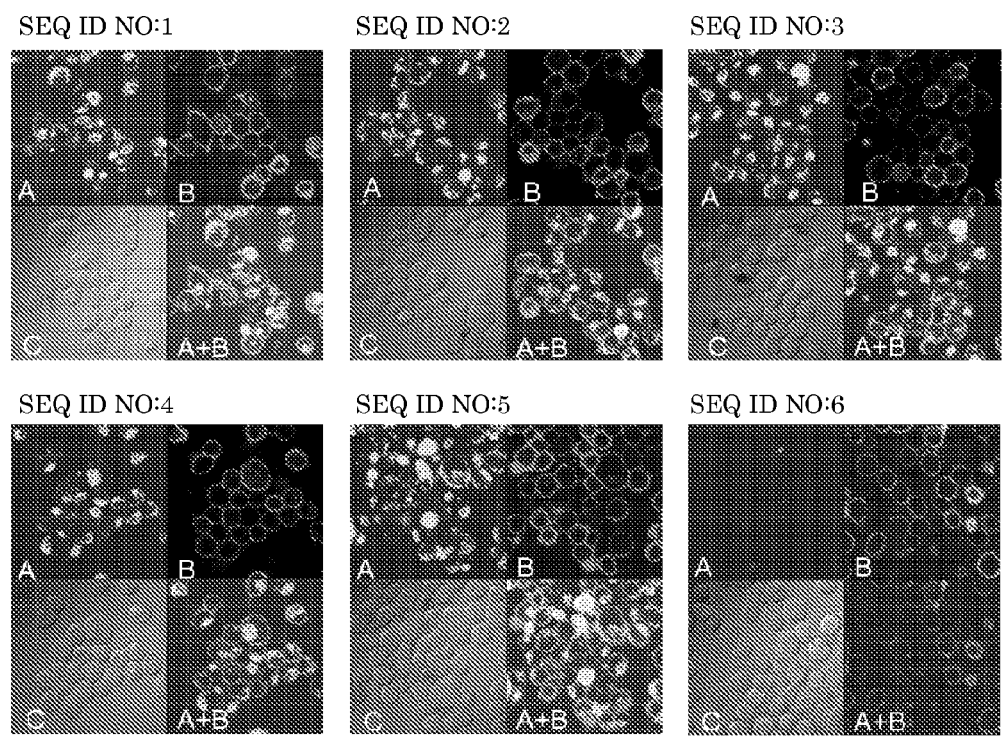
FIG. 12 shows confocal laser microscopic images showing promotion of insulin transfer into HeLa cells by the respective cell-penetrating peptides. In each diagram, A (upper left) shows localization of rhodamine-labeled insulin; B (upper right) shows the cell membrane stained with DiD'Oil; C (lower left) shows a differential interference image; and A+B (lower right) shows a superimposed image of the image A and the image B.

Results of observation using a confocal laser microscope after addition of each of the peptides of SEQ ID NOs:1 to 6 together with rhodamine-labeled insulin are shown in FIG. 12. In contrast to the random peptide of SEQ ID NO:6, which is not a cell-penetrating peptide and did not allow permeation of the rhodamine-labeled insulin into the cells, the cell-penetrating peptides of SEQ ID NOs:1 to 5 of the present invention were confirmed to have allowed permeation of the rhodamine-labeled insulin into the cells.

Example 3

Evaluation of Promotion of Transfer of Polystyrene Beads into Cells

<Method>

In DMEM medium supplemented with 10% FBS, 0.2 ml of HeLa cells were plated on a 96-well glass bottom plate, and the cells were cultured at 37° C. for 48 to 72 hours to allow the cells to adhere to the bottom surface. After 3 times of washing with 200 μl of PBS, 50 μl of DMEM medium containing each of the peptides of SEQ ID NOs:1 to 6 labeled with fluorescein at the amino terminus (contract synthesis by Sigma-Genosys) at a final concentration of 1 μM, fluorescent polystyrene beads (Fluorospheres Carboxylated Microbeads, 0.1 μm; manufactured by Molecular probes, Inc.) at a final concentration of 1 μl/well and 10% FBS was added to each well. The plate was incubated in a CO$_2$ incubator for 3 hours and then washed 3 times with DMEM medium supplemented with 10% FBS, followed by addition of 50 μl of a lysis solution (10 mM Tris-HCl, 5 mM EDTA, 100 mM NaCl, 1% SDS, 100 μg/ml proteinase K) and 1 hour of incubation at room temperature, to decompose the cells. The whole lysis solution was recovered, and the amount of fluorescent polystyrene beads incorporated into the cells was measured using a fluorescence intensity measuring apparatus at an excitation wavelength of 580 nm and a fluorescence wavelength of 605 nm.

<Results>

Figure 3:
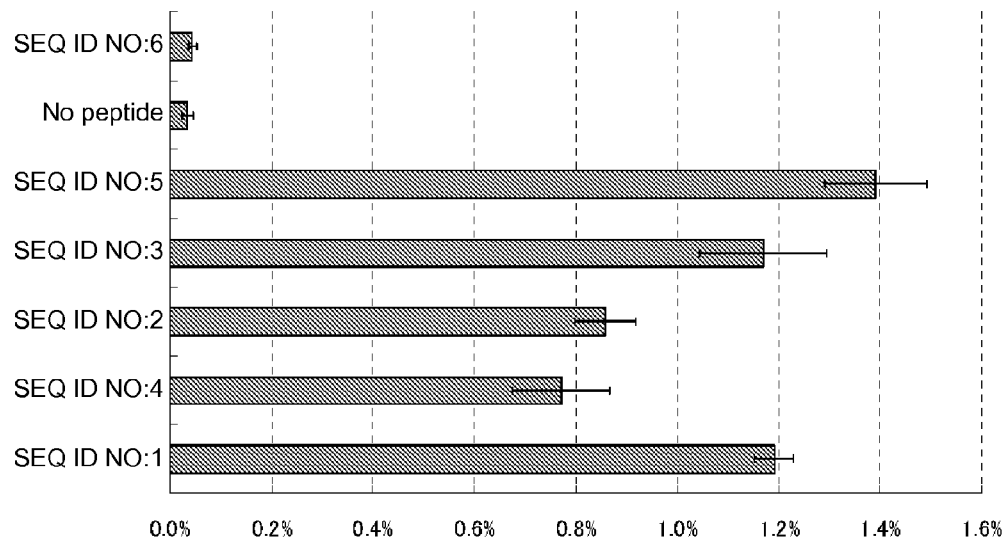
FIG. 3 is a graph showing promotion of transfer of polystyrene beads into HeLa cells by cell-penetrating peptides.

The amount of fluorescent polystyrene beads incorporated into the cells with respect to the amount of fluorescent polystyrene beads added to each well is shown in FIG. 3. For each value, the average value and the standard error obtained by 3 times of evaluation are shown. Although addition of the fluorescent polystyrene beads alone and addition of the beads together with the random peptide of SEQ ID NO:6, which is not a cell-penetrating peptide, to the cells resulted in almost no incorporation of the beads into the cells, addition of the beads together with the peptides of SEQ ID NOs:1 to 5, which are peptides of the present invention, resulted in recovery of not less than 0.7% of the fluorescent polystyrene beads added.

Example 4

Intranasal Administration of Insulin

Figure 4:
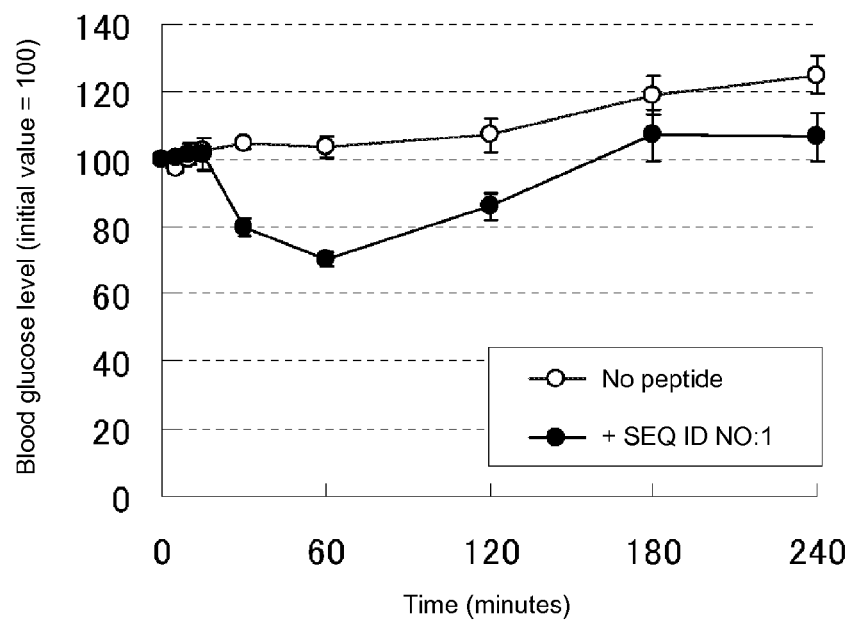
FIG. 4 is a graph showing the blood glucose level as an index of intranasal absorption of insulin, which was observed when a cell-penetrating peptide was used.
Figure 5:
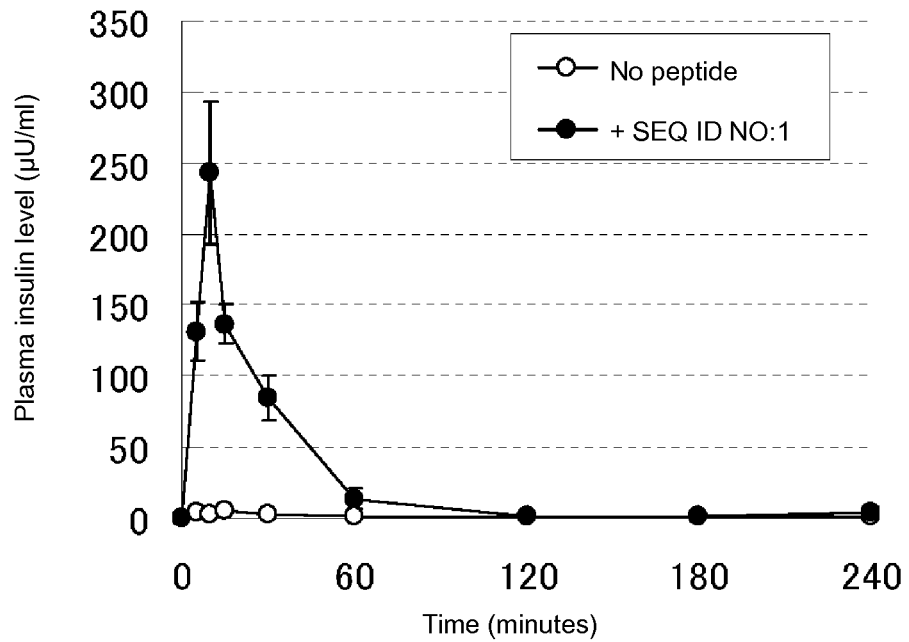
FIG. 5 is a graph showing the plasma insulin level as an index of intranasal absorption of insulin, which was observed when a cell-penetrating peptide was used.

<Method>
A specific amount of insulin (Wako Pure Chemical Industries, Ltd.) powder was placed in a 1.5-ml tube (Eppendorf) and dissolved in 0.1 N HCl, followed by adding the same quantity of 0.1 N NaOH to prepare an insulin solution. A solution of insulin alone, and 40 µl of a mixed solution for each administration experiment were prepared, which mixed solution was prepared by dissolving the peptide of SEQ ID NO:1 whose total amino acid sequence is constituted by amino acids having the configuration of L-body (contract synthesis by Sigma-Genosys) in PBS and combining the resulting solution with the above-mentioned insulin solution such that the mixed solution contains insulin (1 IU/kg) and each peptide at a concentration of 0.5 mM. To a male SD rat having a body weight of about 200 g which had been fasted for 24 hours, 50 mg/kg of pentobarbital was intraperitoneally injected for anesthetization, followed by incision of the neck to expose the trachea. A polyethylene tube (INTRAMEDIC PE205, Clay Adams) was inserted into the trachea, and a part of the esophagus was incised, followed by inserting a tube having the same diameter carefully from the incised portion of the esophagus into a choana such that tissues are not damaged. The tip of the tube to be inserted into the choana was preliminarily sealed with absorbent cotton and an adhesive. To prevent leakage of the drug solution, the nasopalatine canal in the maxillary region opening to the oral cavity is closed with a synthetic adhesive ("Aron alpha A" manufactured by Daiichi-Sankyo Company, Limited). Before the administration, and 5, 10, 15, 30, 60, 120, 180 and 240 minutes after the administration of the prepared mixture of insulin and the peptide, or insulin alone, 0.25 ml of blood was collected from the cervical vein and subjected to measurement of the blood glucose level using a blood glucose level measuring apparatus "Novo Assist Plus" (Novo Nordisk Pharma Ltd.). The remaining blood was subjected to centrifugation for separation of blood plasma, and the plasma insulin level was measured using EIA kit (Revis). The bioavailability was calculated by comparison with the case of subcutaneous administration of insulin.
<Results>
Change in the blood glucose level with time after the administration is shown in FIG. 4, and change in the blood insulin level with time after the administration is shown in FIG. 5. For each value, the average value and the standard error obtained by 3 or 6 times of evaluation are shown. In rats to which only insulin was intranasally administered, increase in the blood insulin level could be hardly confirmed, but in rats to which insulin was administered together with the peptide of SEQ ID NO:1, transfer of insulin into the blood was observed from immediately after the administration. Further, decrease in the blood glucose level, which is a pharmacological activity due to transfer of insulin into the blood, was observed, which decrease in the blood glucose level corresponded to the blood insulin level.

Example 5

Intranasal Administration of Insulin 2

Figure 6:
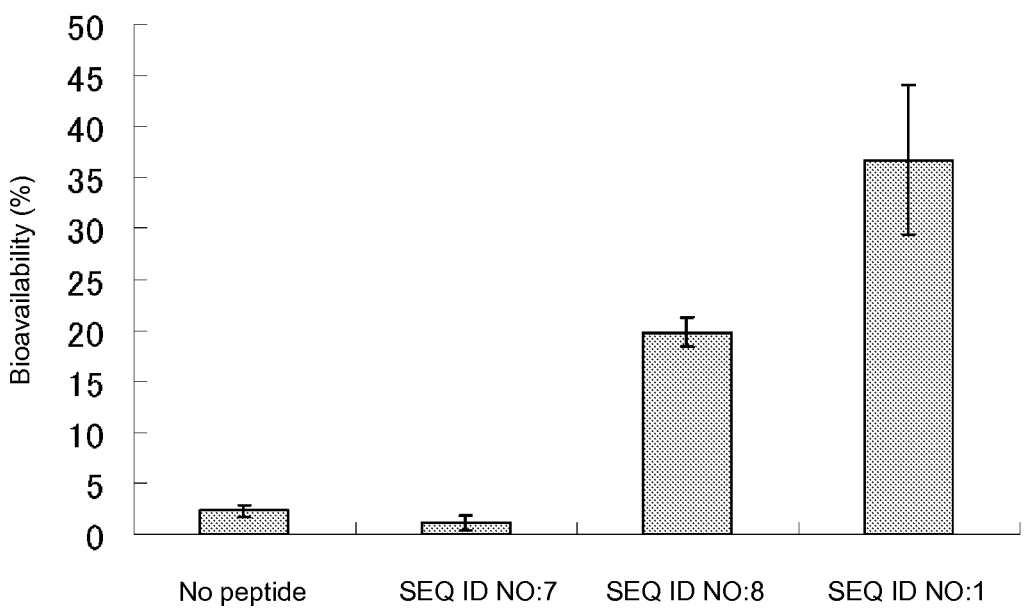
FIG. 6 is a graph showing the bioavailability as an index of intranasal absorption of insulin, which was observed when cell-penetrating peptides were used.

<Method>
Insulin was prepared by the same method as in Example 4, and a solution of insulin alone, and 40 µl of a mixed solution for each administration experiment were prepared, which mixed solution was prepared by dissolving the peptide of SEQ ID NO:1, SEQ ID NO:7 (oligoarginine) or SEQ ID NO:8 (penetratin) whose total amino acid sequence is constituted by amino acids having the configuration of L-body (contract synthesis by Sigma-Genosys) in PBS and combining the resulting solution with the above-mentioned insulin solution such that the mixed solution contains insulin (1 IU/kg) and each peptide at a concentration of 0.5 mM. Each mixed solution was administered to rats by the same method as described in Example 4, and blood collection and measurement were carried out with time, thereby measuring the plasma insulin level, followed by calculating the bioavailability by comparison with the case of subcutaneous administration of insulin
<Results>
The average value and the standard error of the bioavailability calculated by 3 times of evaluation by administration of insulin alone or the mixed solution of insulin and each of the peptides of SEQ ID NOs:1, 7 and 8 are shown in FIG. 6. The cell-penetrating peptide of the present invention having the amino acid sequence represented by SEQ ID NO:1 showed a significantly higher bioavailability than those of the known cell-penetrating peptides represented by SEQ ID NOs:7 and 8.

Example 6

Intranasal Administration of Interferon β

Figure 7:
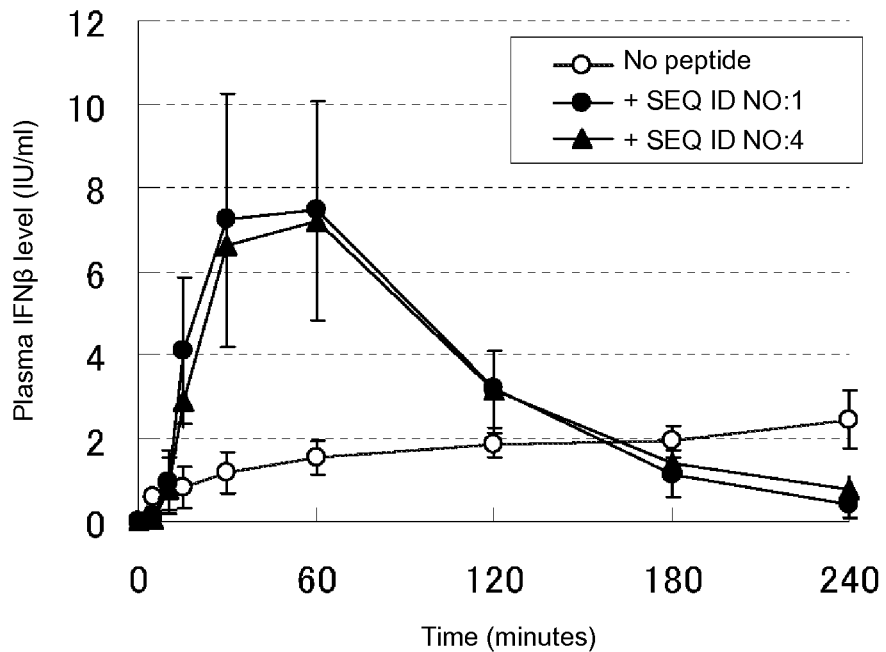
FIG. 7 is a graph showing the plasma interferon-β level as an index of intranasal absorption of interferon-β, which was observed when cell-penetrating peptides were used.

<Method>
With ice cooling, 1 ml of PBS supplemented with Tween 20 was added to human wild-type interferon β ("Feron" manufactured by Toray Industries, Inc.) to attain a concentration of 6,000,000 IU/ml, and 100 µl of this solution was aliquoted, followed by adding 566 µl of PBS supplemented with Tween 20 to the aliquot to prepare a 900,000 IU/ml solution. A solution of interferon β alone, and 40 µl of a mixed solution for each administration experiment were prepared, which mixed solution was prepared by dissolving the peptide of SEQ ID NO:1 or 4 whose total amino acid sequence is constituted by amino acids having the configuration of L-body (contract synthesis by Sigma-Genosys) in PBS and combining the resulting solution with the above-mentioned interferon β solution such that the mixed solution contains interferon β ($0.18 \times 10^6$ IU/kg) and each peptide at a concentration of 0.5 mM. The evaluation was carried out by the same method as described in Example 4. The plasma interferon β level was measured by "human interferon β ELISA kit" (Kamakura Techno-Science Inc.).
<Results>
Change in the plasma interferon β level after the administration is shown in FIG. 7. For each value, the average value and the standard error obtained by 3 times of evaluation are shown. Although rats to which interferon β alone was intranasally administered showed only small increase in the blood interferon β level, rats to which interferon β was administered together with the peptide of SEQ ID NO:1 or SEQ ID NO:4 showed transfer of interferon β into the blood from immediately after the administration.

Example 7

Intranasal Administration of Exendin-4

<Method>

A solution of exendin-4 (contract synthesis by Sigma-Genosys) alone, and 40 μl of a mixed solution for each administration experiment were prepared, which mixed solution was prepared by dissolving the peptide of SEQ ID NO:1 or SEQ ID NO:4 whose total amino acid sequence is constituted by amino acids having the configuration of L-body (contract synthesis by Sigma-Genosys) in PBS and combining the resulting solution with the above-mentioned exendin-4 solution such that the mixed solution contains exendin-4 (0.25 mg/kg) and each peptide at a concentration of 0.5 mM. The evaluation was carried out by the same method as described in Example 4. The plasma exendin-4 level was measured by the sandwich ELISA (enzyme-linked immunosorbent assay) method using an anti-exendin-4 monoclonal antibody as a solid phase, and a biotin-labeled anti-exendin-4 polyclonal antibody and streptavidin-HRP for detection.

<Results>

Figure 8:
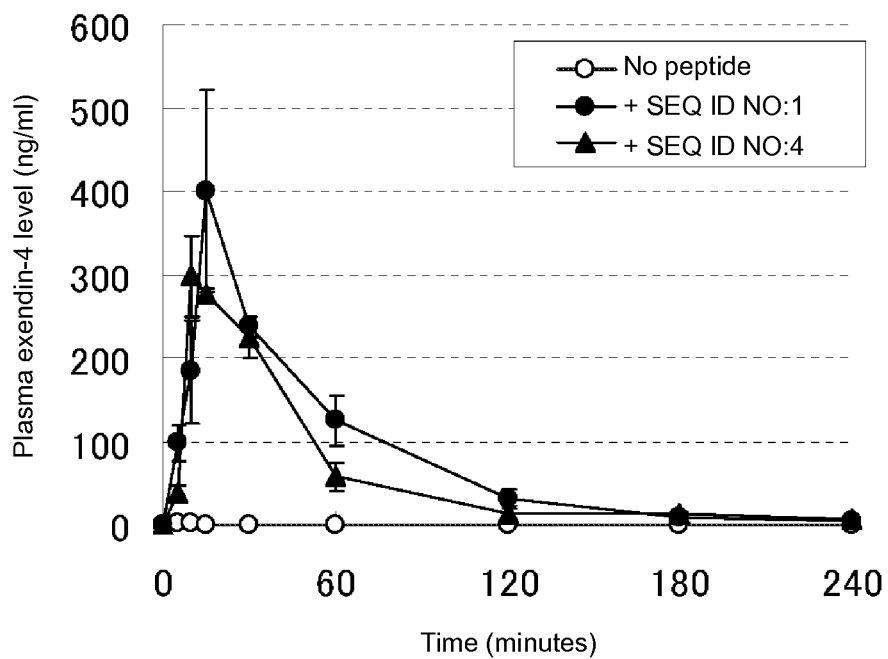
FIG. 8 is a graph showing the plasma exendin-4 level as an index of intranasal absorption of exendin-4, which was observed when cell-penetrating peptides were used.

Change in the plasma exendin-4 level after the administration is shown in FIG. 8. For each value, the average value and the standard error obtained by 3 times of evaluation are shown. Although rats to which only exendin-4 was intranasally administered showed almost no increase in the blood exendin-4 level, rats to which exendin-4 was administered together with the peptide of SEQ ID NO:1 or SEQ ID NO:4 showed transfer of exendin-4 into the blood from immediately after the administration.

Example 8

Intestinal Administration of Insulin

<Method>

An insulin solution was prepared by the same method as in Example 4. A solution of insulin alone, and 500 μl of a mixed solution for each administration experiment were prepared, which mixed solution was prepared by dissolving the peptide of SEQ ID NO:1 or SEQ ID NO:4 whose total amino acid sequence is constituted by amino acids having the configuration of L-body (contract synthesis by Sigma-Genosys) in PBS and combining the resulting solution with the above-mentioned insulin solution such that the mixed solution contains insulin (50 IU/kg) and each peptide at a concentration of 0.5 mM. To a male SD rat having a body weight of about 200 g which had been fasted for 24 hours, 50 mg/kg of pentobarbital was intraperitoncally injected for anesthetization, followed by opening the abdomen in the median line to expose the intestinal tract. A silicone tube was inserted at a position 2 to 3 cm distant from the ileocecal junction toward the ileum, and a feeding needle was inserted at a position about 10 cm upward therefrom. Further, sutures were passed through an area of 6 cm between these. From the feeding needle, 20 ml of phosphate buffered saline (PBS) at pH 7.4 prewarmed to 37° C. was fed at a flow rate of 5 ml/min. to allow discharging of the contents, and the silicone tube was plugged, followed by administering 1 ml of PBS prewarmed to 37° C. from the feeding needle and keeping it retained for 30 minutes. After the administration, the feeding needle was quickly plugged and the intestinal tract was returned into the abdominal cavity, followed by closing the site of incision with a clip and allowing the rat to keep still. After the retention, the plugs of the feeding needle and the silicone tube were removed, and 20 ml of PBS prewarmed to 37° C. was fed into the loop at a flow rate of 5 ml/min. to allow discharging of the contents, followed by ligating the area of 6 cm through which the suture had been preliminarily passed, to form a loop. To this loop, 0.5 ml of the insulin solution alone or the mixture of insulin and the peptide of SEQ ID NO:1 or SEQ ID NO:4 was administered, and the intestinal tract was returned into the abdominal cavity, followed by closing the site of incision with a clip and allowing the rat to keep still. The rat during the experiment was fixed on its back on a hot plate kept at 37° C. by a hot-water circulating pump to regulate the body temperature. Before the administration, and 5, 10, 15, 30, 60, 120 and 180 minutes after the administration, 0.25 ml of blood was collected from the cervical vein and subjected to measurement of the blood glucose level using a blood glucose level measuring apparatus "Novo Assist Plus" (Novo Nordisk Pharma Ltd.). The remaining blood was subjected to centrifugation for separation of blood plasma, and the insulin level was quantified by an enzyme-linked immunosorbent assay. Also for rats to which the same quantity of the insulin solution alone was subcutaneously administered, the blood collection and the measurement were carried out in the same manner.

<Results>

Figure 9:
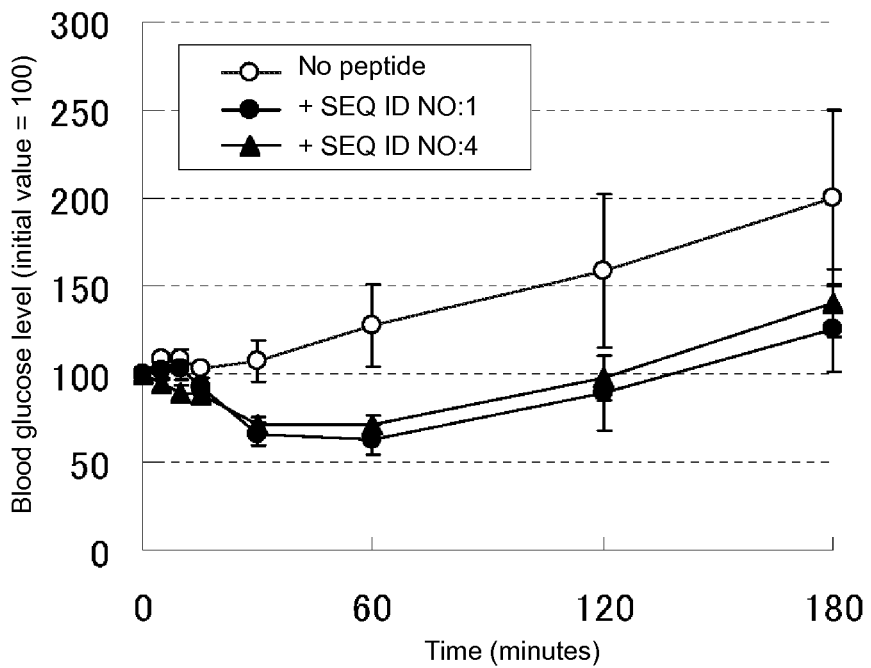
FIG. 9 is a graph showing the blood glucose level as an index of intestinal absorption of insulin, which was observed when cell-penetrating peptides were used.
Figure 10:
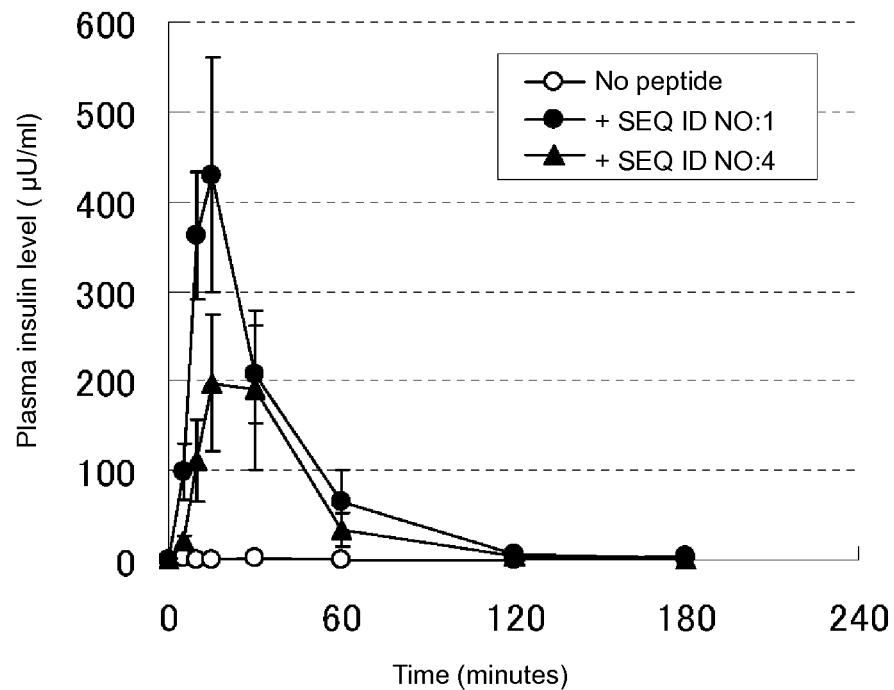
FIG. 10 is a graph showing the plasma insulin level as an index of intestinal absorption of insulin, which was observed when cell-penetrating peptides were used.

Change in the blood glucose level with time after the administration is shown in FIG. 9, and change in the blood insulin level with time after the administration is shown in FIG. 10. For each value, the average value and the standard error obtained by 3 or 6 times of evaluation arc shown. Compared to the case of administration of insulin alone as a control, evident increase in the blood insulin level and evident decrease in the blood glucose level were observed in the cases of combined administration of the peptide of SEQ ID NO:1 or 4 and insulin (FIG. 9 and FIG. 10).

Example 9

Evaluation of Damage to Nasal Cavity

<Method>

By the same method as in Example 4, insulin alone; insulin and the peptide of SEQ ID NO:1; or 5% (w/v) taurodeoxycholic acid solution was intranasally administered. Fifteen minutes later, the nasal cavity was washed with 10 ml of PBS warmed to 37° C. at a flow rate of 2 ml/min. The washing solution was recovered, and the LDH leaked into the solution was measured using LDH activity measuring kit (Pointe Scientific, Inc.).

<Results>

Figure 11:
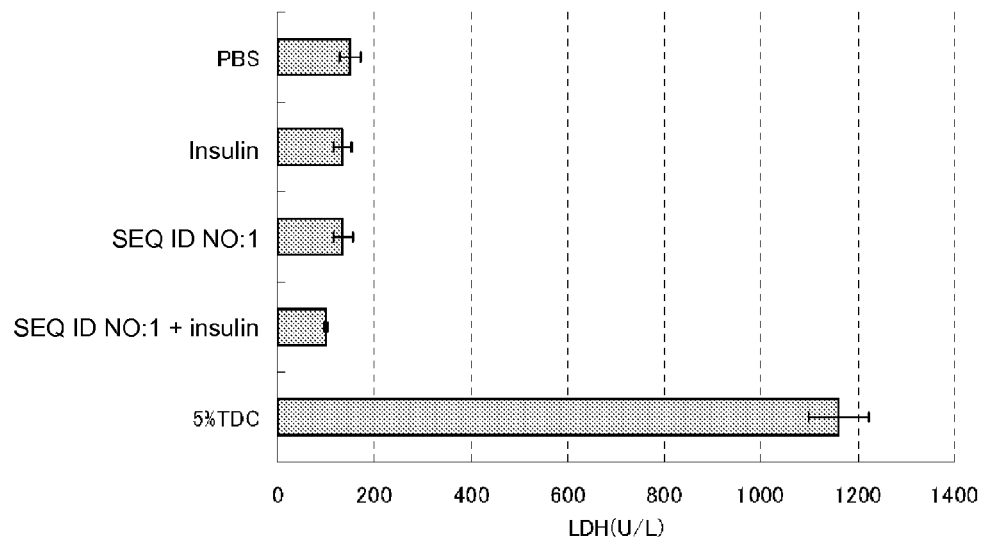
FIG. 11 is a graph showing LDH leakage as an index of intranasal toxicity of a cell-penetrating peptide.

The LDH activity in the washing solution is shown in FIG. 11. For each value, the average value and the standard error obtained by 3 times of evaluation are shown. Compared to the case of administration of 5% (w/v) sodium taurodeoxycholate, release of LDH from the nasal cavity was significantly lower in mice to which the mixed solution of the peptide of SEQ ID NO:1 and insulin was administered, and the release in the latter case was as low as in the cases where PBS or insulin was solely administered.

Example 10

Evaluation of Promotion of Insulin Transfer into Cells 2

<Method>

Evaluation of promotion of insulin transfer into HeLa cells was carried out in the same manner as in Example 2 except that the peptides of SEQ ID NOs:1, 6 and 9 to 11 whose amino termini are not labeled (contract synthesis by Sigma-Genosys) were used. The incubation time in a $CO_2$ incubator was 5 hours, and the amount of rhodamine-labeled insulin incorporated into the cells was measured using a fluorescence intensity measuring apparatus.

<Results>

Figure 13:
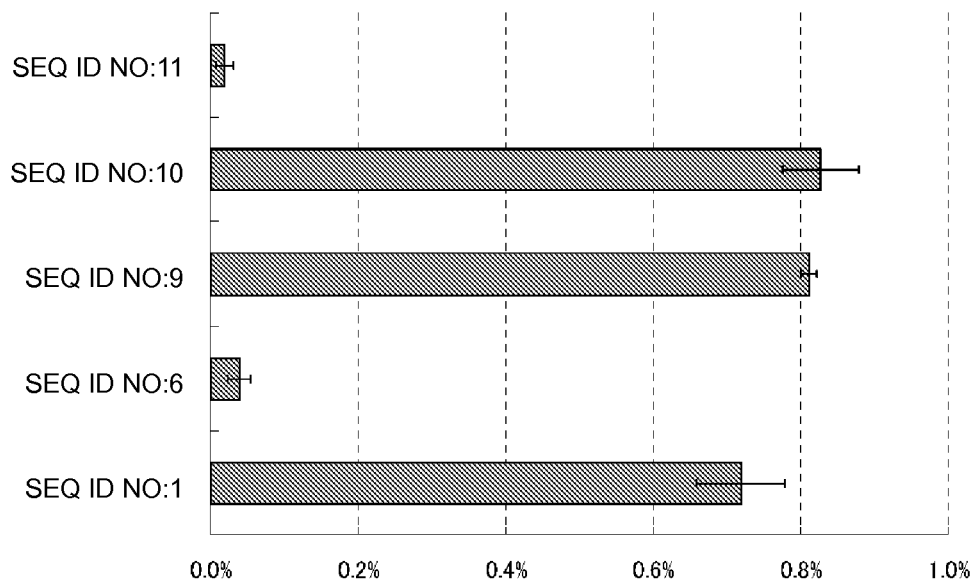
FIG. 13 is a graph showing promotion of insulin transfer into HeLa cells by cell-penetrating peptides.

The amount of rhodamine-labeled insulin incorporated into the cells with respect to the amount of rhodamine-labeled insulin added to each well is shown in FIG. 13. For each value, the average value and the standard error obtained by 3 times of evaluation are shown. In the cases where the random peptide of SEQ ID NO:6 or 11, which had been confirmed not to be a cell-penetrating peptide, was added together to the cells, only not more than 0.05% of the rhodamine-labeled insulin added was incorporated into the cells, while in the cases where the peptide of SEQ ID NO: 1 or SEQ ID NO: 9 or 10 was added together, not less than 0.7% of the rhodamine-labeled insulin added was incorporated into the cells.

Example 11

Intranasal Administration of Insulin 2

<Method>

Insulin was prepared by the same method as in Example 4, and a solution of insulin alone, and 40 µl of a mixed solution for each administration experiment were prepared, which mixed solution was prepared by dissolving the peptide of SEQ ID NO:1, 9 or 10 whose total amino acid sequence is constituted by amino acids having the configuration of L-body (contract synthesis by Sigma-Genosys) in PBS and combining the resulting solution with the above-mentioned insulin solution such that the mixed solution contains insulin (1 IU/kg) and each peptide at a concentration of 0.5 mM. Each mixed solution was administered to rats by the same method as described in Example 4, and blood collection and measurement were carried out with time, thereby measuring the plasma insulin level, followed by calculating the AUC (area under the blood concentration-time curve) based on change in the blood level (µU/ml) with time (minutes).

<Results>

Figure 14:
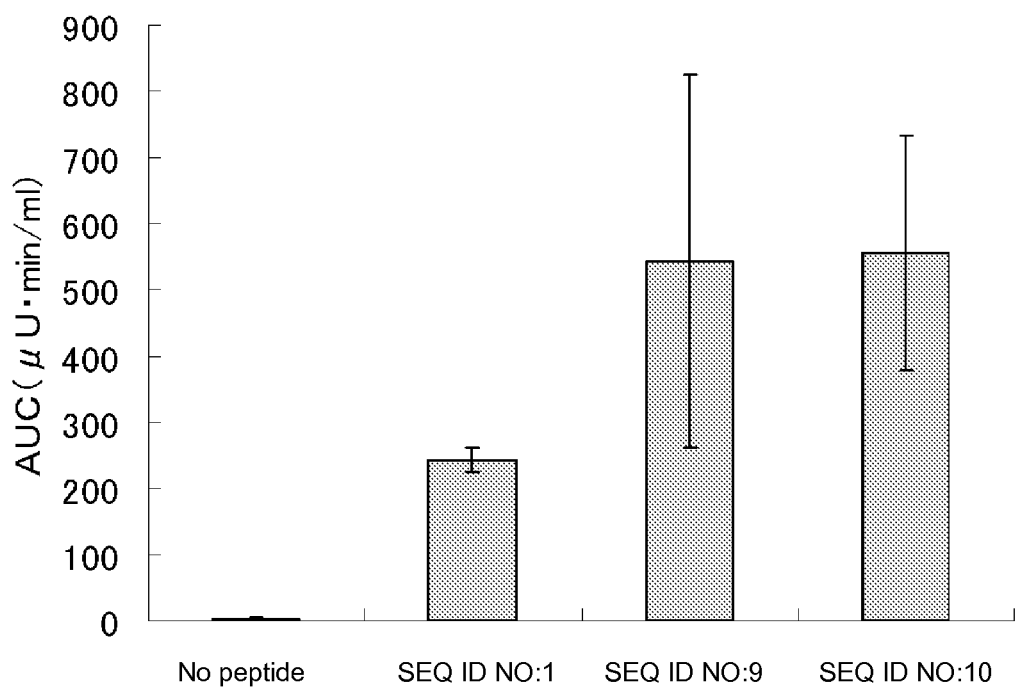
FIG. 14 is a graph showing AUC as an index of intranasal absorption of insulin, which was observed when cell-penetrating peptides were used.

The average value and the standard error of AUC calculated by 3 or 6 times of evaluation wherein insulin alone; or the mixture of the peptide of SEQ ID NO: 1 or SEQ ID NO: 9 or 10 and insulin; was administered are shown in FIG. 14. In the cases where the cell-penetrating peptide of SEQ ID NO: 1, 9 or 10 was administered together with insulin, a significantly higher intranasal absorption of insulin was observed compared to the case where insulin alone was administered.

Example 12

Evaluation of Promotion of Insulin Transfer into Cells 3

<Method>

Evaluation of promotion of insulin transfer into HeLa cells was carried out in the same manner as in Example 2 using the peptides of SEQ ID NO: 6 and 12 to 30 whose amino termini are labeled with fluorescein (contract synthesis by Sigma-Genosys). The incubation time in a $CO_2$ incubator was 5 hours, and the amount of rhodamine-labeled insulin incorporated into the cells was measured using a fluorescence intensity measuring apparatus. Further, the amount of fluorescein incorporated into the cells was measured by the same method as in Example 1.

<Results>

Figure 15:
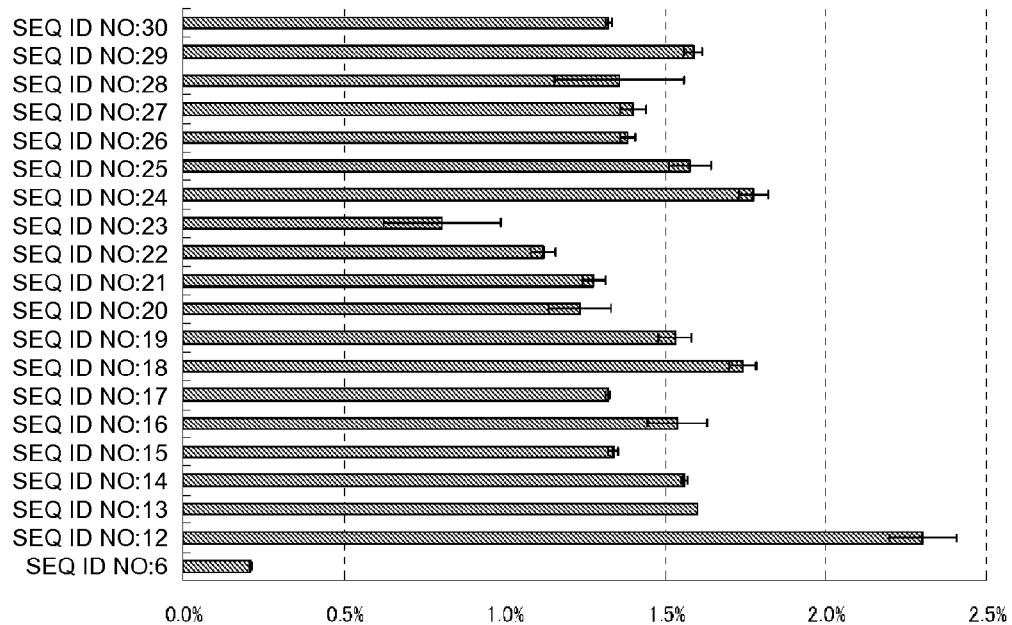
FIG. 15 is a graph showing transfer of cell-penetrating peptides into HeLa cells.

The amount of fluorescein incorporated into the cells with respect to the amount of fluorescein added to each well is shown in FIG. 15. For each value, the average value and the standard error obtained by 2 times of evaluation are shown. Although only about 0.2% of the fluorescein added was incorporated into the cells in the case of the peptide of SEQ ID NO:6 having a random sequence, not less than 0.8% of the fluorescein added was incorporated into the cells in all the cases of the cell-penetrating peptides of SEQ ID NOs:12 to 30 of the present invention.

Figure 16:
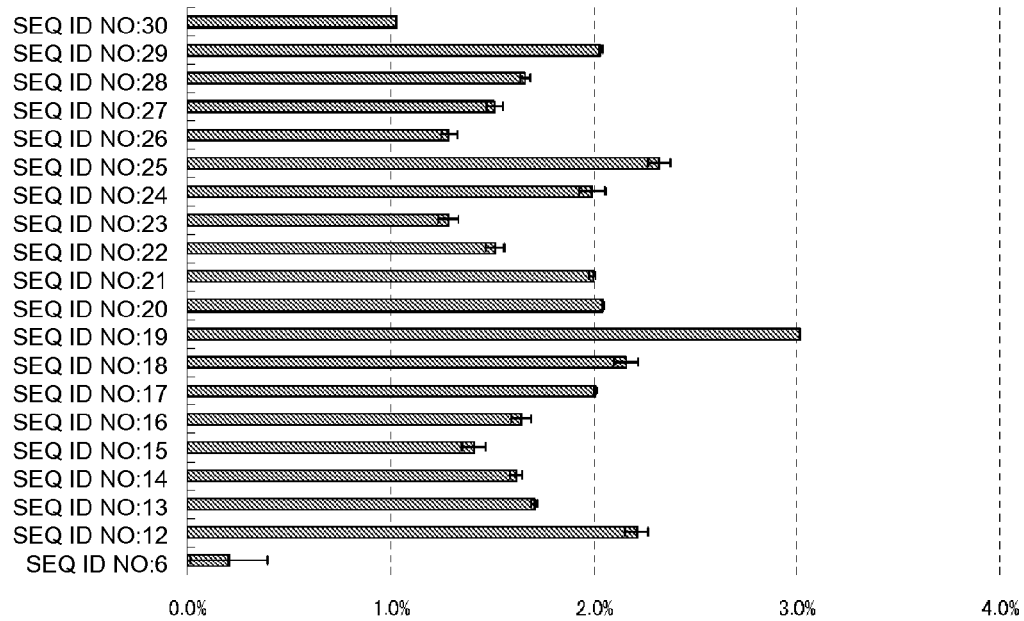
FIG. 16 is a graph showing promotion of insulin transfer into HeLa cells by cell-penetrating peptides.

The amount of rhodamine-labeled insulin incorporated into the cells with respect to the amount of rhodamine-labeled insulin added to each well is shown in FIG. 16. For each value, the average value and the standard error obtained by 2 times of evaluation are shown. Only about 0.2% of the rhodamine-labeled insulin added was incorporated into the cells in the case of the random peptide of SEQ ID NO:6, which is not a cell-penetrating peptide, while not less than 1% was incorporated into the cells in all the cases where the cell-penetrating peptides of SEQ ID NOs:12 to 30 of the present invention were added together with the insulin.

INDUSTRIAL APPLICABILITY

By the present invention, introduction of a hydrophilic physiologically active substance into the cell, which has been difficult so far, becomes possible, and development of a novel medical technology can be expected. More particularly, since a formulation which enables transmucosal administration of a hydrophilic physiologically active substance can be obtained using a cell-penetrating peptide of the present invention, pain and inconvenience of patients, which have been caused by conventional formulations (e.g., injection solutions) comprising hydrophilic physiologically active substances, can be largely improved and hence patient-oriented medical care can be realized at clinical sites. Further, the cell-penetrating peptides of the present invention may fundamentally change the concept of formulations comprising hydrophilic physiologically active substances, leading to creation of epoch-making formulations.

SEQUENCE LISTING FREE TEXT

| SEQUENCE LISTING | |
|---|---|
| SEQ ID NOs: 1 to 5 | Cell-penetrating peptides of the present invention; |
| SEQ ID NO: 6 | Random peptide; |
| SEQ ID NO: 7 | Oligoarginine; |

| SEQ ID NO: 8 | Penetratin |
|---|---|
| SEQ ID NOs: 9 to 10 | Cell-penetrating peptides of the present invention; |
| SEQ ID NO: 11 | Random peptide 2; |
| SEQ ID NOs: 12 to 30 | Cell-penetrating peptides of the present invention. |

The invention claimed is:

1. A cell-penetrating peptide, comprising:
   (A) a peptide having the amino acid sequence of SEQ ID NO:1; or
   (B) a peptide having an amino acid sequence of SEQ ID NO:1 except that up to 3 basic amino acids are substituted with any other basic amino acid, deleted from SEQ ID NO:1, inserted into SEQ ID NO:1 and/or added to SEQ ID NO:1, which peptide has cell membrane permeability.

2. The cell-penetrating peptide according to claim 1, wherein said peptide (B) has the amino acid sequence of any of SEQ ID NOs: SEQ ID NO:2, SEQ ID NO:9, and SEQ ID NO:10.

3. A pharmaceutical composition comprising the cell-penetrating peptide according to claim 1 and a hydrophilic physiologically active substance.

4. The pharmaceutical composition according to claim 3, wherein said hydrophilic physiologically active substance is a peptide, protein or nucleic acid.

5. A method of administering a pharmaceutical composition, which comprises:
   combining the cell-penetrating peptide according to claim 1 and a hydrophilic physiologically active substance into a composition which is pharmaceutically acceptable for nasal or oral administration; and
   administering the pharmaceutically acceptable composition by nasal or oral administration.

* * * * *

```
                      SEQUENCE LISTING

<160> NUMBER OF SEQ ID NOS: 56

<210> SEQ ID NO 1
<211> LENGTH: 16
<212> TYPE: PRT
<213> ORGANISM: Artificial Sequence
<220> FEATURE:
<223> OTHER INFORMATION: Synthetic peptide: original cpps

<400> SEQUENCE: 1

Arg Trp Phe Lys Ile Gln Met Gln Ile Arg Arg Trp Lys Asn Lys Lys
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetic peptide: partially modified r to k

<400> SEQUENCE: 2

Lys Trp Phe Lys Ile Gln Met Gln Ile Lys Lys Trp Lys Asn Lys Lys
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide: partially modified k to r

<400> SEQUENCE: 3

Arg Trp Phe Arg Ile Gln Met Gln Ile Arg Arg Trp Arg Asn Arg Arg
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide: partially modified r to k,
      k to r

<400> SEQUENCE: 4

Lys Trp Phe Arg Ile Gln Met Gln Ile Lys Lys Trp Arg Asn Arg Arg
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide: partially modified reverse

<400> SEQUENCE: 5

Lys Lys Asn Lys Trp Arg Arg Ile Gln Met Gln Ile Lys Phe Trp Arg
1               5                   10                  15
```

```
<210> SEQ ID NO 6
<211> LENGTH: 13
<212> TYPE: PRT
<213> ORGANISM: Artificial Sequence
<220> FEATURE:
<223> OTHER INFORMATION: Synthetic peptide: random peptide

<400> SEQUENCE: 6

Glu Tyr Asp Leu Ser Thr Ala Gly Gly Ala Ala Ala Cys
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide: oligo-arginine

<400> SEQUENCE: 7

Arg Arg Arg Arg Arg Arg Arg Arg
1               5

<210> SEQ ID NO 8
<211> LENGTH: 16
<212> TYPE: PRT
<213> ORGANISM: Drosophila

<400> SEQUENCE: 8

Arg Gln Ile Lys Ile Trp Phe Gln Asn Arg Arg Met Lys Trp Lys Lys
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic peptide: partially modified 1

<400> SEQUENCE: 9

Lys Trp Phe Lys Ile Gln Met Gln Ile Arg Arg Trp Lys Asn Arg Lys
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetic peptide: partially modified 2

<400> SEQUENCE: 10

Lys Trp Phe Lys Ile Gln Met Gln Ile Arg Arg Trp Lys Asn Lys Arg
1               5                   10                  15

<210> SEQ ID NO 11
<211> LENGTH: 20
<212> TYPE: PRT
<213> ORGANISM: Artificial Sequence
<220> FEATURE:
<223> OTHER INFORMATION: Synthetic peptide: random peptide 2

<400> SEQUENCE: 11

Gly Leu Asp Lys Ser Ser Tyr Arg Ile Asp Thr Phe Ala Ala His Glu
1               5                   10                  15

Val Ala Gly Cys
            20
```

```
<210> SEQ ID NO 12
<211> LENGTH: 17
<212> TYPE: PRT
<213> ORGANISM: Artificial Sequence
<220> FEATURE:
<223> OTHER INFORMATION: Synthetic peptide: original cpps and c

<400> SEQUENCE: 12

Arg Trp Phe Lys Ile Gln Met Gln Ile Arg Arg Trp Lys Asn Lys Lys
1               5                   10                  15

Cys

<210> SEQ ID NO 13
<211> LENGTH: 17
<212> TYPE: PRT
<213> ORGANISM: Artificial Sequence
<220> FEATURE:
<223> OTHER INFORMATION: Synthetic peptide: partially modified r tok, k
      to r, and C

<400> SEQUENCE: 13

Lys Trp Phe Arg Ile Gln Met Gln Ile Lys Lys Trp Arg Asn Arg Arg
1               5                   10                  15

Cys

<210> SEQ ID NO 14
<211> LENGTH: 17
<212> TYPE: PRT
<213> ORGANISM: Artificial Sequence
<220> FEATURE:
<223> OTHER INFORMATION: Synthetic peptide: partially modified reverse
      and C

<400> SEQUENCE: 14

Lys Lys Asn Lys Trp Arg Arg Ile Gln Met Gln Ile Lys Phe Trp Arg
1               5                   10                  15

Cys

<210> SEQ ID NO 15
<211> LENGTH: 17
<212> TYPE: PRT
<213> ORGANISM: Artificial Sequence
<220> FEATURE:
<223> OTHER INFORMATION: Synthetic peptide: partially modified 2A and C

<400> SEQUENCE: 15

Arg Ala Phe Lys Ile Gln Met Gln Ile Arg Arg Trp Lys Asn Lys Lys
1               5                   10                  15

Cys

<210> SEQ ID NO 16
<211> LENGTH: 17
<212> TYPE: PRT
<213> ORGANISM: Artificial Sequence
<220> FEATURE:
<223> OTHER INFORMATION: Synthetic peptide: partially modified 3A and C

<400> SEQUENCE: 16

Arg Trp Ala Lys Ile Gln Met Gln Ile Arg Arg Trp Lys Asn Lys Lys
1               5                   10                  15

Cys

<210> SEQ ID NO 17
```

```
<211> LENGTH: 17
<212> TYPE: PRT
<213> ORGANISM: Artificial Sequence
<220> FEATURE:
<223> OTHER INFORMATION: Synthetic peptide: partially modified 5A and C

<400> SEQUENCE: 17

Arg Trp Phe Lys Ala Gln Met Gln Ile Arg Arg Trp Lys Asn Lys Lys
1               5                   10                  15

Cys

<210> SEQ ID NO 18
<211> LENGTH: 17
<212> TYPE: PRT
<213> ORGANISM: Artificial Sequence
<220> FEATURE:
<223> OTHER INFORMATION: Synthetic peptide: partially modified 6A and C

<400> SEQUENCE: 18

Arg Trp Phe Lys Ile Ala Met Gln Ile Arg Arg Trp Lys Asn Lys Lys
1               5                   10                  15

Cys

<210> SEQ ID NO 19
<211> LENGTH: 17
<212> TYPE: PRT
<213> ORGANISM: Artificial Sequence
<220> FEATURE:
<223> OTHER INFORMATION: Synthetic peptide: partially modified 7A and C

<400> SEQUENCE: 19

Arg Trp Phe Lys Ile Gln Ala Gln Ile Arg Arg Trp Lys Asn Lys Lys
1               5                   10                  15

Cys

<210> SEQ ID NO 20
<211> LENGTH: 17
<212> TYPE: PRT
<213> ORGANISM: Artificial Sequence
<220> FEATURE:
<223> OTHER INFORMATION: Synthetic peptide: partially modified 8A and C

<400> SEQUENCE: 20

Arg Trp Phe Lys Ile Gln Met Ala Ile Arg Arg Trp Lys Asn Lys Lys
1               5                   10                  15

Cys

<210> SEQ ID NO 21
<211> LENGTH: 17
<212> TYPE: PRT
<213> ORGANISM: Artificial Sequence
<220> FEATURE:
<223> OTHER INFORMATION: Synthetic peptide: partially modified 9A and C

<400> SEQUENCE: 21

Arg Trp Phe Lys Ile Gln Met Gln Ala Arg Arg Trp Lys Asn Lys Lys
1               5                   10                  15

Cys

<210> SEQ ID NO 22
<211> LENGTH: 17
<212> TYPE: PRT
<213> ORGANISM: Artificial Sequence
<220> FEATURE:
```

```
<223> OTHER INFORMATION: Synthetic peptide: partially modified 12A and C

<400> SEQUENCE: 22

Arg Trp Phe Lys Ile Gln Met Gln Ile Arg Arg Ala Lys Asn Lys Lys
1               5                   10                  15

Cys

<210> SEQ ID NO 23
<211> LENGTH: 17
<212> TYPE: PRT
<213> ORGANISM: Artificial Sequence
<220> FEATURE:
<223> OTHER INFORMATION: Synthetic peptide: partially modified 14A and C

<400> SEQUENCE: 23

Arg Trp Phe Lys Ile Gln Met Gln Ile Arg Arg Trp Lys Ala Lys Lys
1               5                   10                  15

Cys

<210> SEQ ID NO 24
<211> LENGTH: 17
<212> TYPE: PRT
<213> ORGANISM: Artificial Sequence
<220> FEATURE:
<223> OTHER INFORMATION: Synthetic peptide: partially modified 8Q to P
      and c

<400> SEQUENCE: 24

Arg Trp Phe Lys Ile Gln Met Pro Ile Arg Arg Trp Lys Asn Lys Lys
1               5                   10                  15

Cys

<210> SEQ ID NO 25
<211> LENGTH: 17
<212> TYPE: PRT
<213> ORGANISM: Artificial Sequence
<220> FEATURE:
<223> OTHER INFORMATION: Synthetic peptide: partially modified Q to R
      and C

<400> SEQUENCE: 25

Arg Trp Phe Lys Ile Arg Met Arg Ile Arg Arg Trp Lys Asn Lys Lys
1               5                   10                  15

Cys

<210> SEQ ID NO 26
<211> LENGTH: 17
<212> TYPE: PRT
<213> ORGANISM: Artificial Sequence
<220> FEATURE:
<223> OTHER INFORMATION: Synthetic peptide: partially modified head A
      and C

<400> SEQUENCE: 26

Arg Ala Ala Lys Ala Gln Met Gln Ile Arg Arg Trp Lys Asn Lys Lys
1               5                   10                  15

Cys

<210> SEQ ID NO 27
<211> LENGTH: 17
<212> TYPE: PRT
<213> ORGANISM: Artificial Sequence
<220> FEATURE:
<223> OTHER INFORMATION: Synthetic peptide: partially modified tail A
```

-continued and C

<400> SEQUENCE: 27

Arg Trp Phe Lys Ile Gln Ala Gln Ala Arg Arg Ala Lys Asn Lys Lys
1               5                   10                  15

Cys

<210> SEQ ID NO 28
<211> LENGTH: 17
<212> TYPE: PRT
<213> ORGANISM: Artificial Sequence
<220> FEATURE:
<223> OTHER INFORMATION: Synthetic peptide: partially modified IWFM fix
      1 and C

<400> SEQUENCE: 28

Arg Trp Phe Lys Ile Arg Met Lys Ile Arg Gln Trp Gln Asn Lys Lys
1               5                   10                  15

Cys

<210> SEQ ID NO 29
<211> LENGTH: 17
<212> TYPE: PRT
<213> ORGANISM: Artificial Sequence
<220> FEATURE:
<223> OTHER INFORMATION: Synthetic peptide: partially modified IWFM fix
      2 and C

<400> SEQUENCE: 29

Arg Trp Phe Gln Ile Lys Met Arg Ile Gln Arg Lys Asn Lys Lys
1               5                   10                  15

Cys

<210> SEQ ID NO 30
<211> LENGTH: 13
<212> TYPE: PRT
<213> ORGANISM: Artificial Sequence
<220> FEATURE:
<223> OTHER INFORMATION: Synthetic peptide: partially delete and C

<400> SEQUENCE: 30

Phe Lys Ile Gln Met Gln Ile Arg Arg Trp Lys Asn Cys
1               5                   10

<210> SEQ ID NO 31
<211> LENGTH: 16
<212> TYPE: PRT
<213> ORGANISM: Artificial Sequence
<220> FEATURE:
<223> OTHER INFORMATION: Synthetic peptide

<400> SEQUENCE: 31

Lys Trp Phe Lys Ile Gln Met Gln Ile Arg Arg Trp Lys Asn Lys Lys
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Synthetic peptide

<400> SEQUENCE: 32

Arg Trp Phe Arg Ile Gln Met Gln Ile Arg Arg Trp Lys Asn Lys Lys
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Synthetic peptide

<400> SEQUENCE: 33

Arg Trp Phe Lys Ile Gln Met Gln Ile Lys Arg Trp Lys Asn Lys Lys
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Synthetic peptide

<400> SEQUENCE: 34

Arg Trp Phe Lys Ile Gln Met Gln Ile Arg Lys Trp Lys Asn Lys Lys
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Synthetic peptide

<400> SEQUENCE: 35

Arg Trp Phe Lys Ile Gln Met Gln Ile Arg Arg Trp Arg Asn Lys Lys
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Synthetic peptide

<400> SEQUENCE: 36

Arg Trp Phe Lys Ile Gln Met Gln Ile Arg Arg Trp Lys Asn Arg Lys
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Synthetic peptide

<400> SEQUENCE: 37

Arg Trp Phe Lys Ile Gln Met Gln Ile Arg Arg Trp Lys Asn Lys Arg
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Synthetic peptide

<400> SEQUENCE: 38

Lys Trp Phe Lys Ile Gln Met Gln Ile Arg Arg Trp Arg Asn Lys Lys
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Synthetic peptide

<400> SEQUENCE: 39

Lys Trp Phe Lys Ile Gln Met Gln Ile Arg Lys Trp Lys Asn Lys Lys
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Synthetic peptide

<400> SEQUENCE: 40

Lys Trp Phe Lys Ile Gln Met Gln Ile Lys Arg Trp Lys Asn Lys Lys
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Synthetic peptide

<400> SEQUENCE: 41

Lys Trp Phe Arg Ile Gln Met Gln Ile Arg Arg Trp Lys Asn Lys Lys
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Synthetic peptide

<400> SEQUENCE: 42

Arg Trp Phe Arg Ile Gln Met Gln Ile Arg Arg Trp Lys Asn Lys Arg
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Synthetic peptide

<400> SEQUENCE: 43

Arg Trp Phe Arg Ile Gln Met Gln Ile Arg Arg Trp Lys Asn Arg Lys
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Synthetic peptide

<400> SEQUENCE: 44

Arg Trp Phe Arg Ile Gln Met Gln Ile Arg Arg Trp Arg Asn Lys Lys
1               5                   10                  15

```
<210> SEQ ID NO 45
<211> LENGTH: 16
<212> TYPE: PRT
<213> ORGANISM: Artificial Sequence
<220> FEATURE:
<223> OTHER INFORMATION: Synthetic peptide

<400> SEQUENCE: 45

Arg Trp Phe Arg Ile Gln Met Gln Ile Arg Lys Trp Lys Asn Lys Lys
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Synthetic peptide

<400> SEQUENCE: 46

Arg Trp Phe Arg Ile Gln Met Gln Ile Lys Arg Trp Lys Asn Lys Lys
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Synthetic peptide

<400> SEQUENCE: 47

Arg Trp Phe Lys Ile Gln Met Gln Ile Lys Arg Trp Lys Asn Lys Arg
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Synthetic peptide

<400> SEQUENCE: 48

Arg Trp Phe Lys Ile Gln Met Gln Ile Lys Arg Trp Lys Asn Arg Lys
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Synthetic peptide

<400> SEQUENCE: 49

Arg Trp Phe Lys Ile Gln Met Gln Ile Lys Arg Trp Arg Asn Lys Lys
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Synthetic peptide

<400> SEQUENCE: 50

Arg Trp Phe Lys Ile Gln Met Gln Ile Lys Lys Trp Lys Asn Lys Lys
1               5                   10                  15

<210> SEQ ID NO 51
```

```
<211> LENGTH: 16
<212> TYPE: PRT
<213> ORGANISM: Artificial Sequence
<220> FEATURE:
<223> OTHER INFORMATION: Synthetic peptide

<400> SEQUENCE: 51

Arg Trp Phe Lys Ile Gln Met Gln Ile Arg Lys Trp Lys Asn Lys Arg
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Synthetic peptide

<400> SEQUENCE: 52

Arg Trp Phe Lys Ile Gln Met Gln Ile Arg Lys Trp Lys Asn Arg Lys
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Synthetic peptide

<400> SEQUENCE: 53

Arg Trp Phe Lys Ile Gln Met Gln Ile Arg Lys Trp Arg Asn Lys Lys
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Synthetic peptide

<400> SEQUENCE: 54

Arg Trp Phe Lys Ile Gln Met Gln Ile Arg Arg Trp Arg Asn Lys Arg
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Synthetic peptide

<400> SEQUENCE: 55

Arg Trp Phe Lys Ile Gln Met Gln Ile Arg Arg Trp Arg Asn Arg Lys
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Synthetic peptide

<400> SEQUENCE: 56

Arg Trp Phe Lys Ile Gln Met Gln Ile Arg Arg Trp Lys Asn Arg Arg
1               5                   10                  15
```